United States Patent
Li et al.

[11] Patent Number: 6,004,960
[45] Date of Patent: Dec. 21, 1999

[54] PYRIDAZINONES AS INHIBITORS OF CYCLOOXYGENASE-2

[75] Inventors: Chun Sing Li, Pointe Claire; Jacques Y. Gauthier, Laval; Cheuk K. Lau, Ile Bizard; Michel Therien, Laval, all of Canada

[73] Assignee: Merck Frosst Canada, Inc., Kirkland, Canada

[21] Appl. No.: 09/042,174

[22] Filed: Mar. 13, 1998

Related U.S. Application Data

[60] Provisional application No. 60/040,791, Mar. 14, 1997.

[51] Int. Cl.⁶ .................. A61K 31/50; C07D 401/06; C07D 401/12; C07D 237/14
[52] U.S. Cl. .................. 514/247; 544/238; 544/239; 544/240
[58] Field of Search .................. 544/239, 238, 544/240; 514/247

[56] References Cited

U.S. PATENT DOCUMENTS 4,404,203  9/1983  Sircar .......................... 544/239

FOREIGN PATENT DOCUMENTS

| 0 376 079 | 7/1990 | European Pat. Off. |
|---|---|---|
| WO 83/00863 | 3/1983 | WIPO |
| WO 95/00501 | 1/1995 | WIPO |
| WO 95/18799 | 7/1995 | WIPO |
| WO 96/06840 | 3/1996 | WIPO |
| WO 96/24584 | 8/1996 | WIPO |
| WO 96/41626 | 12/1996 | WIPO |
| WO 96/41645 | 12/1996 | WIPO |
| WO 98/03484 | 1/1998 | WIPO |

OTHER PUBLICATIONS

Yane, *Nature*, vol. 367, p. 215–216, 1994.

*Primary Examiner*—Emily Bernhardt
*Attorney, Agent, or Firm*—Richard C. Billups; David L. Rose

[57] ABSTRACT

The invention encompasses the novel compound of Formula I as well as a method of treating cyclooxygenase-2 mediated diseases comprising administration to a patient in need of such treatment of a non-toxic therapeutically effective amount of a compound of Formula I.

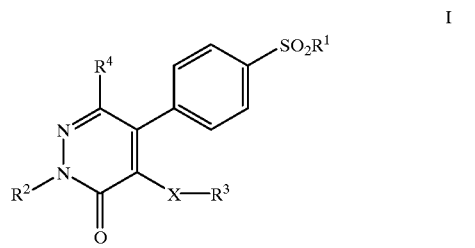

The invention also encompasses certain pharmaceutical compositions for treatment of cyclooxygenase-2 mediated diseases comprising compounds of Formula I.

15 Claims, No Drawings

PYRIDAZINONES AS INHIBITORS OF CYCLOOXYGENASE-2

CROSS REFERENCE TO RELATED APPLICATIONS

This application is a non-provisional application based upon provisional patent application No. 60/040,791 filed on Mar. 14, 1997, priority of which is claimed hereunder.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-I (COX-1) or the in constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

A brief description of the potential utility of cyclooxygenase-2 inhibitors is given in an article by John Vane, Nature, Vol. 367, pp. 215–216, 1994, and in an article in Drug News and Perspectives, Vol. 7, pp. 501–512, 1994.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

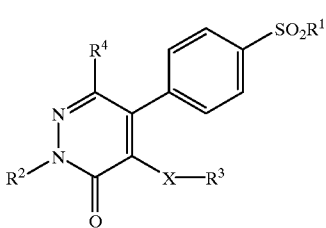

The invention also encompasses certain pharmaceutical compositions for treatment of cyclooxygenase-2 mediated diseases comprising compounds of Formula I.

DETAILED DESCRIPTION OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

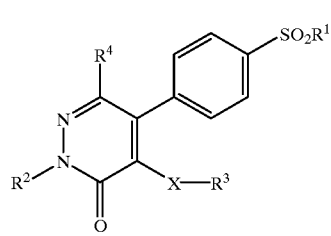

or a pharmaceutically acceptable salt thereof wherein:

X is selected from the group consisting of (a) a bond, (b) (CH2)m, m =1 or 2, (c) CO, (d) O (e) S, and (f) $N(R^5)$, $R^1$ is selected from the group consisting of (a) $CH_3$, (b) $NH_2$, (c) $NHC(O)CF_3$, $R^2$ is selected from the group $(CR^6R^7)_nR^8$, n=0, 1, 2; where $R^6$, $R^7$ are each independently selected from the group consisting of (a) hydrogen, (b) $C_{1-10}$ alkyl, (c) $C_{1-10}$ fluoroalkyl, $R^8$ is selected from the group consisting of (a) $C_{1-10}$alkyl, (b) mono-, di- or tri-substituted phenyl or naphthyl wherein the substituents are selected from the group consisting of (1) hydrogen, (2) halo, (3) $C_{1-10}$alkoxy, (4) $C_{1-10}$alkylthio, (5) CN, (6) $C_{1-6}$ fluoroalkyl (7) $C_{1-10}$ alkyl, (8) $N_3$, (c) mono- , di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, or 3 additional N atoms, wherein the substituents are selected from the group consisting of (1) hydrogen, (2) halo, (3) $C_{1-10}$alkoxy, (4) $C_{1-10}$alkylthio, (5) CN, (6) $C_{1-6}$ fluoroalkyl (7) $C_{1-10}$ alkyl, (8) $N_3$, $R^3$ is selected from the group consisting of
(a) $C_{1-10}$alkyl, (b) mono-, di- or tri-substituted phenyl or naphthyl wherein the substituents are selected from the group consisting of (1) hydrogen, (2) halo, (3) $C_{1-10}$alkoxy, (4) $C_{1-6}$alkylthio, (5) CN, (6) $C_{1-6}$ fluoroalkyl (7) $C_{1-10}$alkyl, (8) $N_3$, (c) mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, or 3 additional N atoms, wherein the substituents are selected from the group consisting of (1) hydrogen, (2) halo, (3) $C_{1-10}$alkoxy, (4) $C_{1-10}$alkylthio, (5) CN, (6) $C_{1-6}$fluoroalkyl (7) $C_{1-10}$alkyl, (8) $N_3$, $R^4$ is selected from the group consisting of (a) hydrogen, (b) halo, (c) $C_{1-6}$alkyl, $R^5$ is selected from the group consisting of (a) hydrogen, (b) $C_{1-6}$alkyl, One preferred embodiment of the invention is that wherein X is bond.

Another preferred embodiment of the invention is that wherein X is O.

Another preferred embodiment of the invention is that wherein $R^1$ is $CH_3$.

Another preferred embodiment of the invention is that wherein $R^4$ is hydrogen.

Another preferred embodiment of the invention is that wherein n is 1.

In another aspect the invention also encompasses a pharmaceutical composition for treating an inflammatory disease susceptable to treatment with an non-steroidal anti-inflammatory agent comprising:

a non-toxic therapeutically effective amount of a compound of formula I and a pharmaceutically acceptable carrier.

In another aspect the invention also encompasses a pharmaceutical composition for treating cyclooxygenase mediated diseases advantageously treated by an active agent that selectively inhibits COX-2 in preference to COX-1 comprising: a non-toxic therapeutically effective amount of a compound of formula I and a pharmaceutically acceptable carrier.

In another aspect the invention also encompasses a method of treating an inflammatory disease susceptable to treatment with an non-steroidal anti-inflammatory agent comprising: administration to a patient in need of such treatment of a non-toxic therapeutically effective amount of a compound of formula I and a pharmaceutically acceptable carrier.

In another aspect the invention also encompasses a method of treating cyclooxygenase mediated diseases advantageously treated by an active agent that selectively inhibits COX-2 in preference to COX-1 comprising:

administration to a patient in need of such treatment of a non-toxic therapeutically effective amount of a compound of formula I.

In another aspect the invention also encompasses the use of a compound of formula I or a pharmaceutical composition in the manufacture of a medicament for the treatment of an inflammatory disease susceptible to treatment with an a non-steroidal anti-inflammatory agent.

The invention is illustrated by the compounds of the Examples disclosed herein as well as the compounds of Table I.

1) Definitions

The following abbreviations have the indicated meanings:

AA=arachidonic acid
Ac=acetyl
AIBN=2.2—-azobisisobutyronitrile
Bn=benzyl
CHO=chinese hamster ovary
CMC=1-cyclohexyl-3-(2-morpholinoethyl) carbodiimidemetho-p-toluenesulfonate
Cox=cyclooxygenase
DBU=diazabicyclo[5.4.0]undec-7-ene
DMAP=4-(dimethylamino)pyridine
DMF=N,N-dimethylformamide
DMSO=dimethyl sulfoxide
$Et_3N$=triethylamine
HBSS=Hanks balanced salt solution
HEPES=N-[2-Hydroxyethyl]piperazine-$N^1$-[2-ethanesulfonic acid]
HWB=human whole blood
IPA=isopropyl alcohol
KHIMDS=potassium hexamethyldisilazane
LDA=lithium diisopropylamide
LPS=lipopolysaccharide
mCPBA=metachloro perbenzoic acid
MMPP=magnesium monoperoxyphthalate
Ms=methanesulfonyl=mesyl
MsO=methanesulfonate=mesylate
NBS=N-bromosuccinimide
NCS=N-chlorosuccinimide
NIS=N-iodosuccinimide
NSAID=non-steroidal anti-inflammatory drug
ODCB=o-dichlorobenzene
Oxone®=potassium peroxymonosulfate
PCC=pyridinium chlorochromate
PDC=pyridinium dichromate
r.t.=room temperature
rac.=racemic
Tf=trifluoromethanesulfonyl=triflyl
TFAA=trifluoroacetic anhydride
Tf=trifluoromethanesulfonate=triflate
THF=tetrahydrofuran
TLC=thin layer chromatography
TMPD=N,N,N',N'-tetramethyl-p-phenylenediamine
Ts=p-toluenesulfonyl=tosyl
TsO=p-toluenesulfonate=tosylate
Tz=1H (or 2H)-tetrazol 5-yl
$SO_2Me$=methyl sulfone (also $SO_2CH_3$)
$SO_2NH_2$=sulfonamide

| Alkyl group abbreviations | Dose Abbreviations |
|---|---|
| Me = methyl | bid = bis in die = twice daily |
| Et = ethyl | qid = quater in die = four times a day |
| n-Pr = normal propyl | id = ter in die = three times a day |
| i-Pr = isopropyl | |
| n-Bu = normal butyl | |
| i-Bu = isobutyl | |
| s-Bu = secondary butyl | |
| t-Bu = tertiary butyl | |
| c-Pr = cyclopropyl | |

| Alkyl group abbreviations | Dose Abbreviations |
|---|---|
| c-Bu = cyclobutyl | |
| c-Pen = cyclopentyl | |
| c-Hex = cyclohexyl | |

For purposes of this specification "Alkyl" means linear branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl- 4-propylnonyl, cyclopropyl, cyclopentyl, cycloheptyl, adamantyl, cyclododecylmethyl, 2-ethyl-1-bicyclo[4.4.0]decyl and the like.

For purposes of this specification "Fluoro alkyl" means alkyl groups in which one or more hydrogen is replaced by fluorine. Examples are —$CF_3$, —$CH_2CH_2F$, —$CH_2CF_3$, c—Pr—$F_5$, c—Hex—$F_{11}$ and the like.

For purposes of this specification "Alkoxy" means alkoxy groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like.

For purposes of this specification "Alkylthio" means alkylthio groups of the indicated number of carbon atoms of a straight, branched or cyclic configuration. Examples of alkylthio groups include methylthio, propylthio, isopropylthio, cycloheptylthio, etc. By way of illustration, the propylthio group signifies —$SCH_2CH_2CH_3$.

For purposes of this specification "Halo" means F, Cl, Br, or I.

Exemplifying the invention are:

(1) 5-(4-Methylsulfonyl)phenyl-2-phenyl-4-phenyl-2H-pyridazin-3-one,
(2) 2-Methyl-5-(4-methylsulfonyl)phenyl-4-phenyl-2H-pyridazin-3-one,
(3) 2-Cyclopropylmethyl-5-(4-methylsulfonyl)phenyl-4-phenyl-2H-pyridazin-3-one,
(4) 5-(4-Methylsulfonyl)phenyl-4-phenyl-2-(2,2,2-trifluoroethyl)-2H-pyridazin-3-one,
(5) 2-Benzyl-5-(4-methylsulfonyl)phenyl-4-phenyl-2H-pyridazin-3-one,
(6) 2-Isopropyl-5-(4-methylsulfonyl)phenyl-4-phenyl-2H-pyridazin-3-one,
(7) 2-Cyclopropylmethyl-4-(3,4-difluorophenyl)-5-(4-methylsulfonyl)phenyl-2H-pyridazin-3-one,
(8) 5-(4-Methylsulfonyl)phenyl-4-phenyl-2-(2-pyridylmethyl)-2H-pyridazin-3-one,
(9) 2-Benzyl-4-(3,4-difluorophenyl)-5-(4-methylsulfonyl)phenyl-2H-pyridazin-3-one,
(10) 2-(4-Fluorobenzyl)-5-(4-methylsulfonyl)phenyl-4-phenyl-2H-pyridazin-3-one,
(11) 2-Carbomethoxymethyl-5-(4-methylsulfonyl)phenyl-4-phenyl-2H-pyridazin-3-one,
(12) 2-Benzyl-4-(4-fluorophenyl)-5-(4-methylsulfonyl)phenyl-2H-pyridazin-3-one,
(13) 2-(4-Carbomethoxybenzyl)-5-(4-methylsulfonyl)phenyl-4-phenyl-2H-pyridazin-3-one,
(14) 2-Cyclopropylmethyl-4-(4-fluorophenyl)-5-(4-methylsulfonyl)phenyl-2H-pyridazin-3-one,
(15) 2-(3-Fluorobenzyl)-5-(4-methylsulfonyl)phenyl-4-phenyl-2H-pyridazin-3-one,
(16) 2-(4-Fluorobenzyl)- 4-(4-fluorophenyl)-5-(4-methylsulfonyl)phenyl-2H-pyridazin-3-one,
(17) 2-(2-Fluorobenzyl)-5-(4-methylsulfonyl)phenyl-4-phenyl-2H-pyridazin-3-one,
(18) 2-Cyclopropyl-5-(4-methylsulfonyl)phenyl-4-(4-fluorophenyl)-2H-pyridazin-3-one,
(19) 4-(4-Fluorophenyl)-5-(4-methylsulfonyl)phenyl-2-(3,3,3-trifluoropropyl)-2H-pyridazin-3-one,
(20) 4-(4-Fluorophenyl)-5-(4-methylsulfonyl)phenyl-2-(4-pyridylmethyl)-2H-pyridazin-3-one,
(21) 2-Benzyl-4-(2-propoxy)-5-(4-methylsulfonyl)phenyl-2H-pyridazin-3-one,
(22) 2-Benzyl-4-(4-fluorophenoxy)-5-(4-methylsulfonyl)phenyl-2H-pyridazin-3-one,
(23) 2-Benzyl-4-(5-chloro-2-pyridyloxy)-5-(4-methylsulfonyl)phenyl-2H-pyridazin-3-one,
(24) 2-(2,2-Dimethylpropyl)-4-(4-fluorophenyl)-5-(4-methylsulfonyl)phenyl-2H-pyridazin-3-one,
(25) 4-(4-Fluorophenyl)-5-(4-methylsulfonyl)phenyl-2-(1-phenyl-ethyl)-2H-pyridazin-3-one,
(26) 2-(3-Fluorophenyl)-5-(4-methylsulfonyl)phenyl-4-phenyl-2H-pyridazin-3-one,
(27) 4-(4-Fluorophenyl)-5-(4-methylsulfonyl)phenyl-2-(thiophen-2-yl-methyl)-2H-pyridazin-3-one,
(28) 2-Benzyl-5-(4-methylsulfonyl)phenyl-4-(3-pyridyl)-2H-pyridazin-3-one,
(29) 4-(4-Fluorophenyl)-5-(4-methylsulfonyl)phenyl-2-(4,4,4-trifluorobutyl)-2H-pyridazin-3-one,
(30) 2-Benzyl-4-(6-methyl-3-pyridyl)-5-(4-methylsulfonyl)phenyl-2H-pyridazin-3-one,
(31) 4-(4-Fluorophenyl)-2-(2-methylpropyl)-5-(4-methylsulfonyl)phenyl-2H-pyridazin-3-one,
(32) 2-Cyclobutylmethyl-4-(4-fluorophenyl)-5-(4-methylsulfonyl)phenyl-2H-pyridazin-3-one,
(33) 2-(2-Phenethyl)-4-(4-fluorophenyl)-5-(4-methylsulfonyl)phenyl-2H-pyridazin-3-one,
(34) 2-Benzyl-4-(5-bromo-2-pyridyloxy)-5-(4-methylsulfonyl)phenyl-2H-pyridazin-3-one,
(35) 2-Benzyl-4-(4-methylphenyl)-5-(4-methylsulfonyl)phenyl-2H-pyridazin-3-one, and
(36) 2-Cyclohexylmethyl-4-(4-fluorophenyl)-5-(4-methylsulfonyl)phenyl-2H-pyridazin-3-one.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of formula I as described above.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising:
administration to a patient in need of such treatment of a non-toxic therapeutically effective amount of a compound of Formula I as disclosed herein.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like, and basic ion exchange resins.

It will be understood that in the discussion of methods of treatment which follows, references to the compounds of Formula I are meant to also include the pharmaceutically acceptable salts.

The compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis) and for the treatment of glaucoma.

By virtue of its high cyclooxygenase-2 (COX-2) activity and/or its specificity for cyclooxygenase-2 over cyclooxygenase-1 (COX-1), Compound I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a prostaglandin including misoprostol, enprostil, rioprostil, ornoprostol or rosaprostol; a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. No. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxy-ethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-todic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods Method A An appropriately 3-substituted 5-hydroxy-4-(4-methylsulfonyl)phenyl-5H-furan-2-one II (WO 9636623) is reacted with hydrazine in an alcoholic solvent such as ethanol under refusing condition to give the intermediate III, which is subsequently alkylated with an appropriate electrophile in the presence of an alkaline base such as sodium hydroxide in a solvent auch as DMF to afford pyridazinone IV.

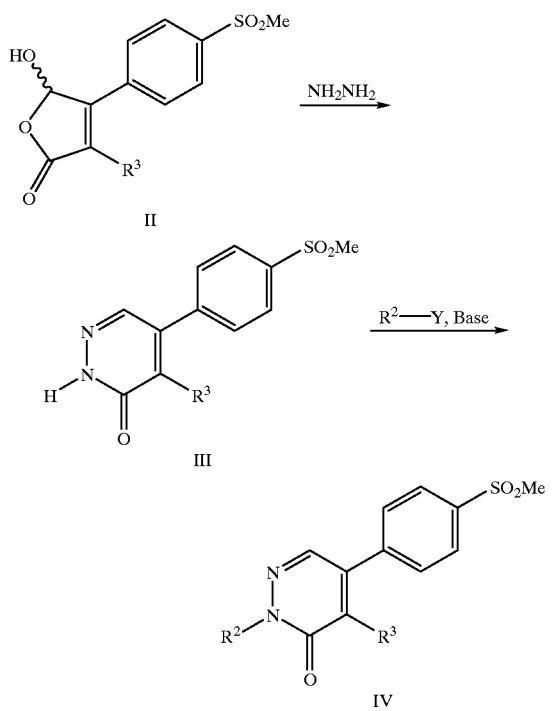

Y = halogen, sulfonate

Method B

An appropriately 3-substituted 5-hydroxy-4-(4-methylsulfonyl)phenyl-5H-furan-2-one II is reacted with an appropriately substituted hydrazine or its hydrochloride salt in an alcoholic solvent such as ethanol under refluxing condition to afford pyridazinone IV.

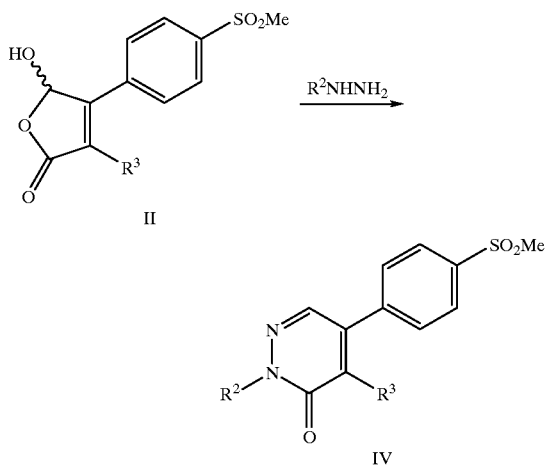

Method C

An appropriately 3-substituted-4-(methylsulfonyl) phenyl-5H-furan-2-one V (WO 9500501) is brominated by NBS in a chlorinated solvent or bromine in HOAc. The bromide VI is transformed to the hydroxy intermediate II in THF-H20 with catalytic amount of acid such as HOAc under refluxing condition. The intermediate II is then converted to the pyridazinone IV followed by Method A or Method B.

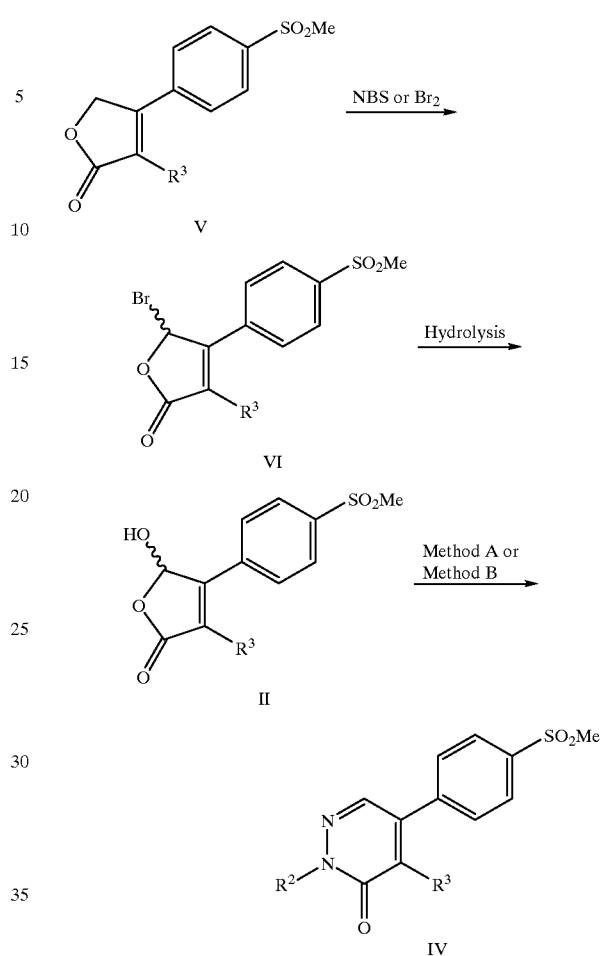

Method D

4,5-Dibromo-2H-pyridazin-3-one VII is alkylated with an appropriate electrophile in the presence of an alkaline base such as cesium carbonate or sodium hydroxide in a solvent such as DMF. The alkylated intermediate VIII is then reacted with an alkaline hydroxide under phase transfer condition to give the hydroxy intermediate IX. The corresponding triflate of IX is prepared under conventional condition and then coupled with 4-(methylthio)phenyl boronic acid in the presence of a palladium (0) catalyst and a base such as sodium carbonate and followed by oxidation with mCPBA or MMPP to give the mono-bromo intermediate X. Coupling of X with an appropriate boronic acid in the presence of a palladium (0) catalyst and a base such as sodium carbonate affords the pyridazinone IV.

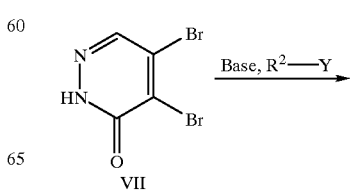

-continued

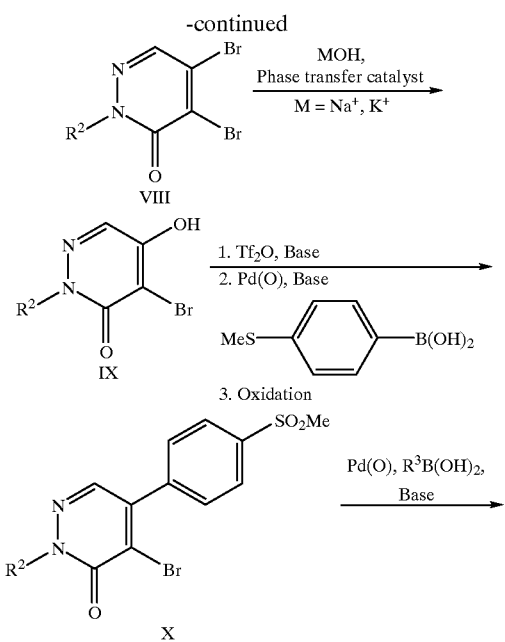

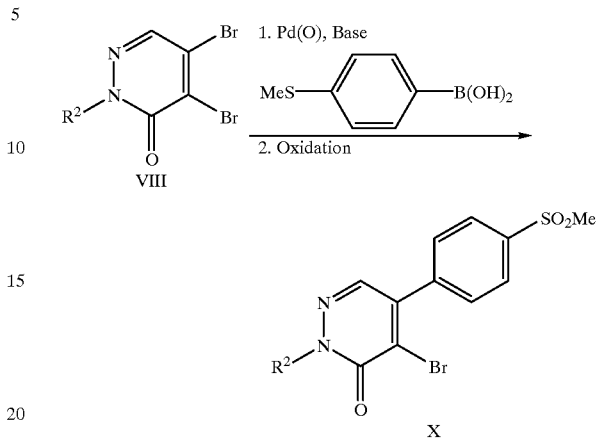

Method E

An appropriately substituted 4-bromo-2H-pyridazin-3-one X is reacted with an appropriate nucleophile in the presence of an alkaline base such as cesium carbonate to afford pyridazinone I.

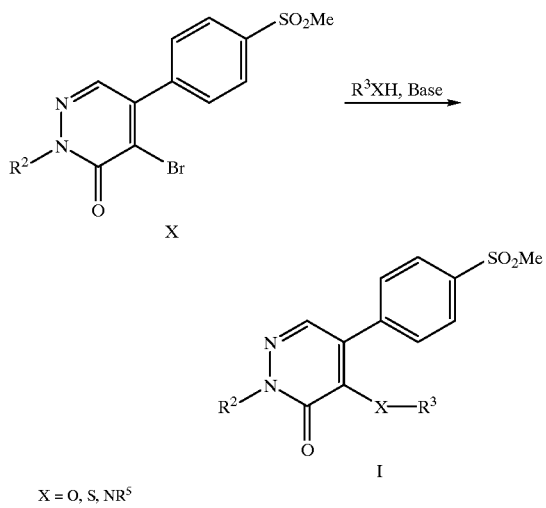

Method F

The mono-bromo intermediate X is also prepared by the palladium (0) catalysed coupling of 4-(methylthio)phenyl boronic acid with the dibromo intermediate VIII to give a mixture of the desired regio-isomer, the other regio-isomer and the bis-coupling product. The desired regio-isomer is separated by flash column chromatography and followed by oxidation with an oxidizing agent such as mCPBA, Oxone or MMPP to afford intermediate X.

Method G

Tetronic acid XI is converted to the bromolactone XII by the treatment with oxalyl bromide and then coupled with 4-(methylthio)phenyl boronic acid in the presence of a palladium (0) catalyst and a base such as sodium carbonate to give the intermediate XIII. Bromination of XIII in a solvent such as $CH_2C_{12}$ followed by oxidation with an oxidizing agent such as MMPP provides the 3-bromolactone XIV. The 3-bromolactone XIV is then brominated with NBS in a chlorinated solvent such as $CHCl_3$ and subsequently hydrolysed the 5-bromo intermediate in THF-H20 with catalytic amount of acid such as HOAc to afford the 5-hydroxy-3-bromolactone XV. The lactone XV is reacted with hydrazine in refluxing alcoholic solvent such as EtOH to give the 4-bromo-5-(4-methylsulfonyl)phenyl-2H-pyridazin-3-one XVI. Reaction with an appropriate eletrophile provides the 4-bromo-pyridazinone intermediate X.

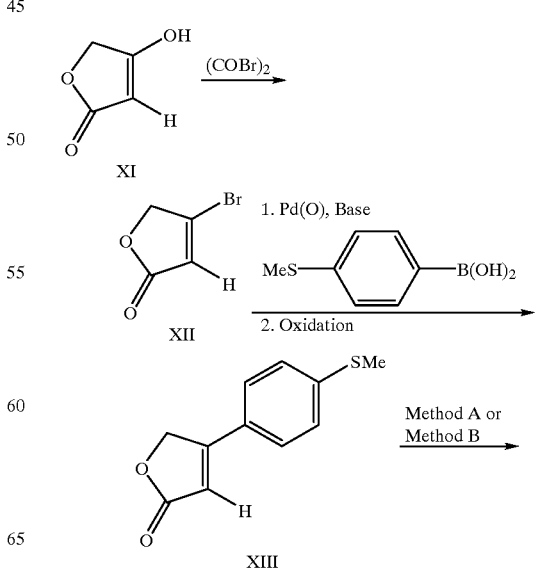

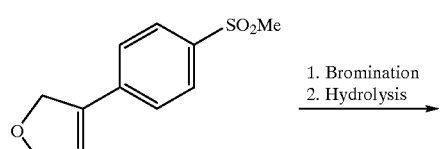
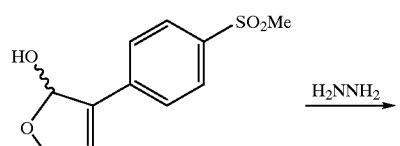
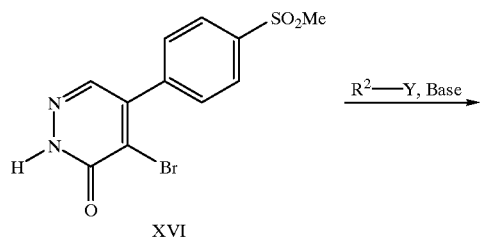
Representative Compounds
Tables I illustrates novel compounds of the present invention.
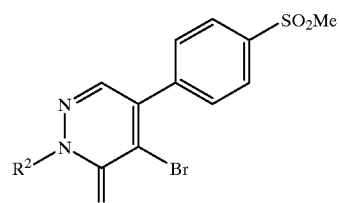
TABLE I
| Structure | Example | Method |
|---|---|---|
| (5-(4-methylsulfonylphenyl)-2,6-diphenylpyridazin-3(2H)-one) | 1 | B |
| (2-methyl-5-(4-methylsulfonylphenyl)-6-phenylpyridazin-3(2H)-one) | 2 | B |
| (2-(cyclopropylmethyl)-5-(4-methylsulfonylphenyl)-6-phenylpyridazin-3(2H)-one) | 3 | A |

TABLE I-continued

| Structure | Example | Method |
|---|---|---|
| 2-(2,2,2-trifluoroethyl)-5-(4-methylsulfonylphenyl)-4-phenyl-pyridazin-3(2H)-one | 4 | B |
| 2-benzyl-5-(4-methylsulfonylphenyl)-4-phenyl-pyridazin-3(2H)-one | 5 | A |
| 2-isopropyl-5-(4-methylsulfonylphenyl)-4-phenyl-pyridazin-3(2H)-one | 6 | A |
| 2-(cyclopropylmethyl)-5-(4-methylsulfonylphenyl)-4-(3,4-difluorophenyl)-pyridazin-3(2H)-one | 7 | A |
| 2-(2-pyridylmethyl)-5-(4-methylsulfonylphenyl)-4-phenyl-pyridazin-3(2H)-one | 8 | A |
| 2-benzyl-5-(4-methylsulfonylphenyl)-4-(3,4-difluorophenyl)-pyridazin-3(2H)-one | 9 | A |

TABLE I-continued

| Structure | Example | Method |
|---|---|---|
| 2-(4-fluorobenzyl)-4-phenyl-5-[4-(methylsulfonyl)phenyl]-3(2H)-pyridazinone | 10 | A |
| 2-(methoxycarbonylmethyl)-4-phenyl-5-[4-(methylsulfonyl)phenyl]-3(2H)-pyridazinone | 11 | A |
| 2-benzyl-4-(4-fluorophenyl)-5-[4-(methylsulfonyl)phenyl]-3(2H)-pyridazinone | 12 | A |
| 2-[4-(methoxycarbonyl)benzyl]-4-phenyl-5-[4-(methylsulfonyl)phenyl]-3(2H)-pyridazinone | 13 | A |
| 2-(cyclopropylmethyl)-4-(4-fluorophenyl)-5-[4-(methylsulfonyl)phenyl]-3(2H)-pyridazinone | 14 | A |
| 2-(3-fluorobenzyl)-4-phenyl-5-[4-(methylsulfonyl)phenyl]-3(2H)-pyridazinone | 15 | A |

TABLE I-continued

| | Example | Method |
|---|---|---|
| 4-(4-fluorobenzyl), 5-(4-methylsulfonylphenyl), 4-(4-fluorophenyl)pyridazin-3(2H)-one | 16 | A |
| 2-(2-fluorobenzyl), 5-(4-methylsulfonylphenyl), 4-phenylpyridazin-3(2H)-one | 17 | A |
| 2-cyclopropyl, 5-(4-methylsulfonylphenyl), 4-(4-fluorophenyl)pyridazin-3(2H)-one | 18 | B |
| 2-(3,3,3-trifluoropropyl), 5-(4-methylsulfonylphenyl), 4-(4-fluorophenyl)pyridazin-3(2H)-one | 19 | A |
| 2-(pyridin-4-ylmethyl), 5-(4-methylsulfonylphenyl), 4-(4-fluorophenyl)pyridazin-3(2H)-one | 20 | A |
| 2-benzyl, 5-(4-methylsulfonylphenyl), 4-isopropoxypyridazin-3(2H)-one | 21 | E |

TABLE I-continued

| Example | Method |
|---|---|
| 22 | E |
| 23 | E |
| 24 | A |
| 25 | A |
| 26 | B |
| 27 | A |

TABLE I-continued
| | Example | Method |
|---|---|---|
| 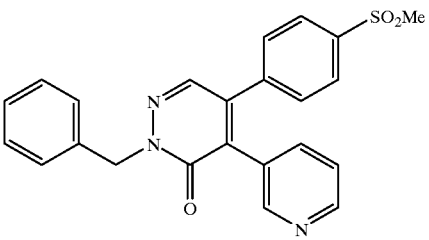 | 28 | D |
| 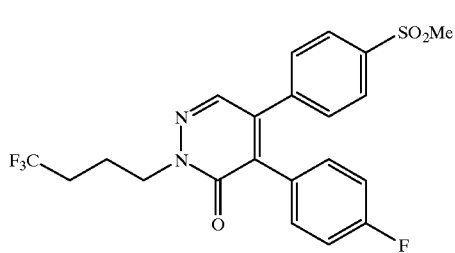 | 29 | A |
| 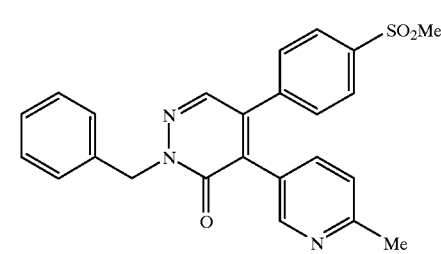 | 30 | D |
| 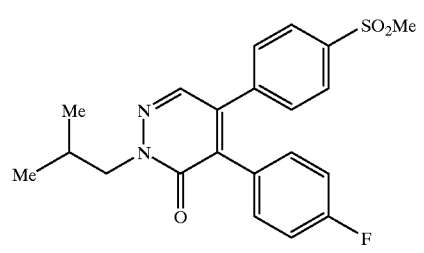 | 31 | A |
| 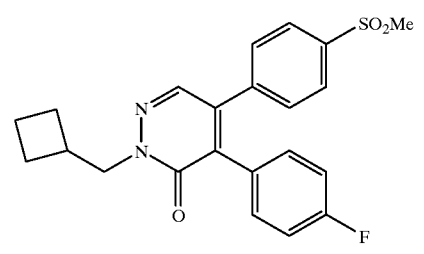 | 32 | A |
| 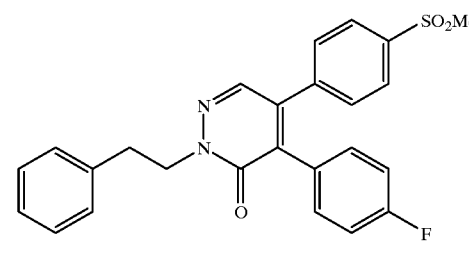 | 33 | A |

TABLE I-continued

| | Example | Method |
|---|---|---|
| (structure: 2-benzyl-5-(4-methylsulfonylphenyl)-4-(5-bromopyridin-2-yloxy)pyridazin-3(2H)-one) | 34 | E |
| (structure: 2-benzyl-5-(4-methylsulfonylphenyl)-4-(4-methylphenyl)pyridazin-3(2H)-one) | 35 | D |
| (structure: 2-cyclohexylmethyl-5-(4-methylsulfonylphenyl)-4-(4-fluorophenyl)pyridazin-3(2H)-one) | 36 | A |
| (structure: 2-cyclopropylmethyl-5-(4-methylsulfonylphenyl)-4-(5-chloropyridin-2-yloxy)pyridazin-3(2H)-one) | 37 | |
| (structure: 2-cyclopropylmethyl-5-(4-methylsulfonylphenyl)-4-isopropoxypyridazin-3(2H)-one) | 38 | |
| (structure: 2-benzyl-5-(4-methylsulfonylphenyl)-4-(phenylthio)pyridazin-3(2H)-one) | 39 | |

TABLE I-continued

| | Example | Method |
|---|---|---|
| (structure: 2-benzyl-5-(4-methylsulfonylphenyl)-4-(cyclopropylmethoxy)pyridazin-3(2H)-one) | 40 | |
| (structure: 2-benzyl-5-(4-methylsulfonylphenyl)-4-((2-methylcyclopropyl)methoxy)pyridazin-3(2H)-one) | 41 | |
| (structure: 2-benzyl-5-(4-methylsulfonylphenyl)-4-(cyclopentyloxy)pyridazin-3(2H)-one) | 42 | |
| (structure: 2-benzyl-5-(4-methylsulfonylphenyl)-4-((2-fluorocyclopentyl)oxy)pyridazin-3(2H)-one) | 43 | |
| (structure: 2-benzyl-5-(4-methylsulfonylphenyl)-4-((2,2-difluorocyclopentyl)oxy)pyridazin-3(2H)-one) | 44 | |
| (structure: 2-benzyl-5-(4-methylsulfonylphenyl)-4-(pyridin-2-yl)pyridazin-3(2H)-one) | 45 | |

TABLE I-continued

| Example | Method |
|---|---|
| 46 | |
| 47 | |
| 48 | |
| 49 | |
| 50 | |
| 51 | |

TABLE I-continued

| | Example | Method |
|---|---|---|
| 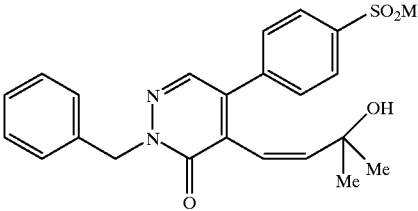 | 52 | |
| 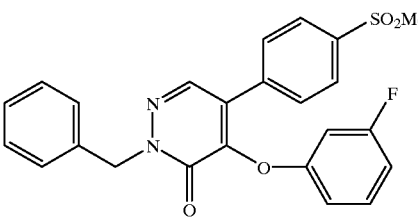 | 53 | |
| 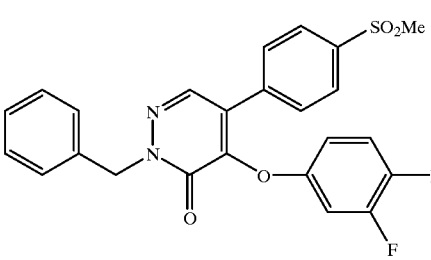 | 54 | |

Assays for determining Biological Activity

The compound of Formula I can be tested using the following assays to determine their cyclooxygenase-2 inhibiting activity.

INHIBITION OF CYCLOOXYGENASE ACTIVITY

Whole cell assays for COX-2 and COX-1 using CHO transfected cell lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-21 cells prepared by trypsinization of adherent cultures are harvested by centrifugation (300×g, 10 min) and washed once in HBSS containing 15 mM HEPES, pH 7.4, and resuspended in HBSS, 15 mM HEPES, pH 7.4, at a cell concentration of $1.5 \times 10^6$ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells ($0.3 \times 10^6$ cells in 200 p) are preincubated with 3 AIl of the test drug or DMSO vehicle for 15 min at 37° C. Working solutions of peroxide-free AA (5.5 pM and 110 gM AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 $\mu$M AA in the CHOhCOX-1] assay and a final concentration of 10 $\mu$M AA in the CHO [hCOX-2] assay. The reaction is terminated by the addition of 10 pl 1 N HCI followed by neutralization with 20 $\mu$l of 0.5 N NaOH. The samples are centrifuged at 300×g at 4° C. for 10 min, and an aliquot of the clarified supernatant is appropriately diluted for the determination of $PGE_2$ levels using an enzyme-liked immunoassay for PGE2 (Correlate $PGE_2$ enzyme immunoassay kit, Assay Designs, Inc.). Cyclooxygenase activity in the absence of test compounds is determined as the difference in $PGE_2$ levels of cells challenged with arachidonic acid versus the $PGE_2$ levels in cells mock-challenged with ethanol vehicle. Inhibition of PGE2 synthesis by test compounds is calculated as a percentage of the activity in the presence of drug versus the activity in the positive control samples.

Assay of COX-1 Activity from U937 cell microsomes

U 937 cells are pelleted by centrifugation at 500×g for 5 min and washed once with phosphate-buffered saline and repelleted. Cells are resuspended in homogenization buffer consisting of 0.1 M Tris-HCl, pH 7.4, 10 mM EDTA, 2 $\mu$g/ml leupeptin, 2 $\mu$g/ml soybean trypsin inhibitor, 2 tg/ml aprotinin and 1 mM phenyl methyl sulfonyl fluoride. The cell suspension is sonicated 4 times for 10 sec and is centrifuged at 10,000×g for 10 min at 4° C. The supernatant is centrifuged at 100,000×g for 1 hr at 4° C. The 100,000×g microsomal pellet is resuspended in 0.1 M Tris-HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 $\mu$g/ml in 0.1 M Tris-HCl buffer, pH 7.4 containing 10 mM EDTA, 0.5 mM phenol, 1 mM reduced glutathione and 1 $\mu$M hematin. Assays are performed in duplicate in a final volume of 250 pl. Initially, 5 pl of DMSO vehicle or drug in DMSO are added to 20 μl of 0.1 M Tris-HCl buffer, pH 7.4 containing 10 mM EDTA in wells of a 96-deepwell polypropylene titre plate. 200 μl of the microsomal preparation are then added and pre-incubated for 15 min at room temperature before addition of 25 μl of 1 M arachidonic acid in 0.1 M Tris-HCl and 10 mM EDTA, pH 7.4. Samples are incubated for 40 min at room temperature and the reaction is stopped by the addition of 25 pl of 1 N HCl. Samples are neutralized with 25 μl of 1 N NaOH prior to quantitation of $PGE_2$ content by radioimmunoassay (Dupont-NEN or Amersham assay kits). Cyclooxygenase activity is defined as the difference between PGE2 levels in samples incubated in the presence of arachidonic acid and ethanol vehicle.

Assay of the activity of purified human COX-2

The enzyme activity is measured using a chromogenic assay based on the oxidation of N,N,N',N'-tetramethyl-p-phenylenediamine (TMPD) during the reduction of PGG2 to PGH2 by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 μL) contains 100 mM sodium phosphate, pH 6.5, 2 mM genapol X-100, 1 gM hematin, 1 mg(ml gelatin, 80–100 units of purified enzyme (One unit of enzyme is defined as the amount of enzyme required to produce an O.D. change of 0.001/min at 610 nm) and 4 μL of the test compound in DMSO. The mixture is pre-incubated at room temperature (22° C.) for 15 minutes prior to initiation of the enzymatic reaction by the addition of 20 μL of a sonicated solution of 1 mM arachidonic acid (AA) and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D./min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on PGE2 production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of PGE2 after LPS induction (COX-2) and $T1B_2$ following blood clotting (COX-1) in the same assay.

Method

A. COX-2 (LPS-induced PGE2 production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2mL blood aliquot to use as blank (basal levels of $PGE_2$). The remaining blood is incubated with LPS (100 μg/ml final concentration, Sigma Chem, #L-2630 from E. coli; diluted in 0.1% BSA (Phosphate buffered saline) for 5 minutes at room temperature. Five hundred μL aliquots of blood are incubated with either 2μL of vehicle (DMSO) or 2 μL of a test compound at final concentrations varying from 10nM to 30 μM for 24 hours at 37° C. At the end of the incubation, the blood is centrifuged at 12,000×g for 5 minutes to obtain plasma. A 100 μL aliquot of plasma is mixed with 400 μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood is collected into vacutainers containing no anticoagulants. Aliquots of 500 μL are immediately transferred to siliconized microcentrifuge tubes preloaded with 2 μL of either DMSO or a test compound at final concentrations varying from 10nM to 30 μM. The tubes are vortexed and incubated at 37° C. for 1 hour to allow blood to clot. At the end of incubation, serum is obtained by centrifugation (12,000×g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 ml of 1% carrageenan solution in saline (FMC Corp, Maine) into the paw using an insulin syringe with a 25-gauge needle (i.e. 500 mg carrageenan per paw). Three hr later, the paw volume ($V_3$) is measured and the increases in paw volume ($V_3$—$V_O$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

LPS-Induced Pyrexia in Conscious Rats

Male Sprague-Dawley rats (150–200 g) were fasted for 16–18 -h before use. At approximately 9:30 a.m., the animals were placed temporarily in plexiglass restrainers and their baseline rectal temperature was recorded using a flexible temperature probe (YSI series 400) connected to a digital thermometer (Model 08502, Cole Parmer). The same probe and thermometer were used for all animals to reduce experimental error. The animals were returned to their cages after the temperature measurements. At time zero, the rats were injected intraperitoneally with either saline or LPS (2 mg/kg, Sigma Chem) and the rectal temperature was remeasured at 5, 6 and 7 h following LPS injection. After the measurement at 5 h, when the increase in temperature had reached a plateau, the LPS-injected rats were given either the vehicle (1% methocel) or a test compound orally to determine whether the compound could reverse the pyrexia.

Percent reversal of the pyrexia was calculated using the rectal temperature obtained at 7 h in the control (vehicle-treated) group as the reference (zero reversal) point. Complete reversal of pyrexia to the pre-LPS baseline value is taken as 100%.

LPS-Induced Pyrexia in Conscious Squirrel Monkeys

Temperature probes were surgically implanted under the abdominal skin in a group of squirrel monkeys (*Saimiri sciureus*) (1.0–1.7 kg). This allows for the monitoring of body temperature in conscious, unrestrained monkeys by a telemetric sensing system (Data Sciences International, Minnesota). The animals were fasted and were placed in individual cages for acclimatization 13–14 h before use. Electronic receivers were installed on the side of the cages which pick up signals from the implanted temperature probes. At approximately 9:00 a.m. on the day of the experiment, the monkeys were restrained temporarily in training chairs and were given a bolus I.V. injection of LPS, (6 mg/kg, dissolved in sterile saline). The animals were returned to their cages and body temperature was recorded continuously every 5 min. Two h after injection of LPS, when the body temperature had increased by 1.5–2∞C, the monkeys were dosed orally with either vehicle (1% methocel) or a test compound (3 mg/kg). One hundred minutes later, the difference between the body temperature and the baseline value was determined. Percent inhibition was calculated taking the value in the control group as 0% inhibition.

Acute Inflammatory Hyperalgesia Induced by Carrageenan in Rats

Experiments were performed using male Sprague Dawley rats (90–110 g). Hyperalgesia to mechanical compression of the hind paw was induced by intraplantar injection of carrageenan (4.5 mg into one hind paw) 3 h previously. Control animals received an equivalent volume of saline (0.15 ml intraplantar). A test compound (0.3–30 mg/kg, suspended in 0.5% methocel in distilled water) or vehicle (0.5% methocel) was administered orally (2ml/kg) 2 h after carrageenan. The vocalisation response to compression of the hind paw was measured 1 h later using a Ugo Basile algesiometer.

Statistical analysis for carrageenan-induced hyperalgesia was performed using one-way ANOVA (BMDP Statistical Software Inc.). Hyperalgesia was determined by subtracting the vocalisation threshold in saline injected rats from that obtained in animals injected with carrageenan. Hyperalgesia scores for drug-treated rats were expressed as a percentage of this response. $ID_{50}$ values (the dose producing 50% of the maximum observed response) were then calculated by non-linear least squares regression analysis of mean data using GraFit (Erithacus Software).

Adjuvant-Induced Arthritis in Rats

Seventy, 6.5–7.5 week old, female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of Mycobacterium butyricum in 0.1 ml of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day -1) and 21 days following adjuvant injection, and primary paw volumes were determined before (day -1) and on days 4 and 21 following adjuvant injection. The rats were anesthetized with an intramuscular injection of 0.03–0.1 ml of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subehondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, Indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

Two-factor ('treatment' and 'time') analysis of variance with repeated measures on 'time' were applied to the % changes for body weight and foot volumes and to the rank-transformed radiographic total scores. Apost hoc Dunnett's test was conducted to compare the effect of treatments to vehicle. A one-way analysis of variance was applied to the thymic and spleen weights followed by the Dunnett's test to compare the effect of treatments to vehicle. Dose-response curves for % inhibition in foot volumes on days 4, 14 and 21 were fitted by a 4-parameter logistic function using a non-linear least squares' regression. $ID_{50}$ was defined as the dose corresponding to a 50% reduction from the vehicle and was derived by interpolation from the fitted 4-parameter equation.

PHARMACOKINETICS IN RATS

Per Os Pharmacokinetics in Rats

PROCEDURE:

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1h, 2h, 4h, 6h

After the 4 hr time point bleed, food is provided to the rats ad libitum. Water is provided at all times during the study.
Vehicles:

The following vehicles may be used in PO rat blood level determinations:

PEG 200/300/400: restricted to 2 mL/kg

Methocel 0.5%–1.0%: 10 mL/kg

Tween 80: 10 mL/kg

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h•kg (milliliters per hour kilogram)

Intravenous Pharmacokinetics in Rats
PROCEDURE:

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1h, 2h, 6h or 0, 5 min, 30 min, 1h, 2h, 4h, 6h.
Vehicles:

The following vehicles may be used in IV rat blood level determinations:

Dextrose: 1 mL/kg

Moleculosol 25%: 1 mL/kg

DMSO (dimethylsulfoxide): Restricted to a dose volume of 0.1 mL per animal

PEG 200: Not more than 60% mixed with 40% sterile water—1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h•kg (milliliters per hour kilogram)

NSAID-INDUCED GASTROPATHY IN RATS
Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In -the present assay, NSMID-induced gastrointestinal damage is observed by measuring fecal $^{51}$Cr excretion after systemic injection of $^{51}$Cr-labeled red blood cells. Fecal $^{51}$Cr excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}$Cr-labeled red blood cells from a donor rat. The animals are placed individually in metabolism cages with food and water ad lib. Feces are collected for a 48 h period and $^{51}$Cr fecal excretion is calculated as a percent of total injected dose. $^{51}$Cr-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 Ci of sodium $^{51}$chromate for 30 min. at 37C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5Ci/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

Representative Biological Data

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-I or cyclooxygenase-2 and a putative inhibitor. The $IC_{50}$ values represent the concentration of putative inhibitor required to return $PGE_2$ synthesis to 50% of that obtained as compared to the uninhibited control.

The results for certain of the biological assays may be seen in Table II.

TABLE II

| Example Number | Structure | COX-2 ($IC_{50}$ μM) | | COX-1 ($IC_{50}$ μM) |
|---|---|---|---|---|
| | | CHO | HWB | U-937 HWB |
| 1 | | 0.08 | 4.7 | >10 |
| 2 | | 0.7 | 21 | >10 |
| 3 | | 0.07 | 1.3 | >10 |
| 4 | | 0.5 | 11.1 | >10 |

TABLE II-continued

| Example Number | Structure | COX-2 (IC$_{50}$ μM) CHO | COX-2 (IC$_{50}$ μM) HWB | COX-1 (IC$_{50}$ μM) U-937 | COX-1 (IC$_{50}$ μM) HWB |
|---|---|---|---|---|---|
| 5 | 2-benzyl-5-(4-methylsulfonylphenyl)-4-phenyl-pyridazin-3(2H)-one | 0.03 | 1.0 | >10 | >50 |
| 6 | 2-isopropyl-5-(4-methylsulfonylphenyl)-4-phenyl-pyridazin-3(2H)-one | 0.6 | 2.6 | >10 | |
| 7 | 2-cyclopropylmethyl-4-(3,4-difluorophenyl)-5-(4-methylsulfonylphenyl)-pyridazin-3(2H)-one | 0.16 | 3.2 | >10 | |
| 8 | 2-(pyridin-2-ylmethyl)-5-(4-methylsulfonylphenyl)-4-phenyl-pyridazin-3(2H)-one | ~2 | >33 | >10 | |
| 9 | 2-benzyl-4-(3,4-difluorophenyl)-5-(4-methylsulfonylphenyl)-pyridazin-3(2H)-one | 0.04 | 1.9 | 3–10 | |

TABLE II-continued

| Example Number | Structure | COX-2 (IC$_{50}$ μM) CHO | COX-2 (IC$_{50}$ μM) HWB | COX-1 (IC$_{50}$ μM) U-937 | COX-1 (IC$_{50}$ μM) HWB |
|---|---|---|---|---|---|
| 10 | | 0.17 | 0.9 | >10 | |
| 11 | | 5 | 9.2 | >10 | |
| 12 | | 0.03 | 0.8 | 3–10 | |
| 13 | | 2.0 | >33 | >10 | |
| 14 | | 0.18 | 1.7 | >10 | |
| 15 | | 0.009 | 0.8 | >10 | |

TABLE II-continued

| Example Number | Structure | COX-2 (IC$_{50}$ μM) CHO | COX-2 (IC$_{50}$ μM) HWB | COX-1 (IC$_{50}$ μM) U-937 | COX-1 (IC$_{50}$ μM) HWB |
|---|---|---|---|---|---|
| 16 | | 0.053 | 1.1 | 3–10 | |
| 17 | | 0.03 | 1.7 | >10 | |
| 18 | | 0.11 | >33 | ~10 | |
| 19 | | 0.09 | 3.1 | >10 | |
| 20 | | 1.4 | 16.8 | >10 | |
| 21 | | 0.016 | 1.7 | >10 | >100 |

TABLE II-continued

| Example Number | Structure | COX-2 (IC$_{50}$ μM) CHO | COX-2 (IC$_{50}$ μM) HWB | COX-1 (IC$_{50}$ μM) U-937 | COX-1 (IC$_{50}$ μM) HWB |
|---|---|---|---|---|---|
| 22 | 2-benzyl-5-(4-methylsulfonylphenyl)-4-(4-fluorophenoxy)pyridazin-3(2H)-one | 0.02 | 0.09 | 0.3–1 | 9.0 |
| 23 | 2-benzyl-5-(4-methylsulfonylphenyl)-4-(5-chloropyridin-2-yloxy)pyridazin-3(2H)-one | 0.26 | 0.9 | 3–10 | |
| 24 | 2-neopentyl-5-(4-methylsulfonylphenyl)-4-(4-fluorophenyl)pyridazin-3(2H)-one | 0.16 | 2.4 | ~10 | |
| 25 | 2-(1-phenylethyl)-5-(4-methylsulfonylphenyl)-4-(4-fluorophenyl)pyridazin-3(2H)-one | 0.49 | 1.4 | ~1 | |
| 26 | 2-(3-fluorophenyl)-5-(4-methylsulfonylphenyl)-4-phenylpyridazin-3(2H)-one | 0.065 | 5.5 | >10 | |
| 27 | 2-(thiophen-2-ylmethyl)-5-(4-methylsulfonylphenyl)-4-(4-fluorophenyl)pyridazin-3(2H)-one | 0.054 | <0.4 | ~1 | |

TABLE II-continued

| Example Number | Structure | COX-2 (IC$_{50}$ μM) CHO | COX-2 (IC$_{50}$ μM) HWB | COX-1 (IC$_{50}$ μM) U-937 | COX-1 (IC$_{50}$ μM) HWB |
|---|---|---|---|---|---|
| 28 | | 0.13 | 1.5 | >10 | 56 |
| 29 | | 0.18 | 1.3 | >10 | |
| 30 | | 1.2 | 1.1 | >10 | |
| 31 | | 0.18 | 3.8 | >10 | |
| 32 | | 0.029 | 0.56 | ~10 | |
| 33 | | — | 8.6 | >10 | |

TABLE II-continued

| Example Number | COX-2 (IC$_{50}$ μM) | | COX-1 (IC$_{50}$ μM) | |
|---|---|---|---|---|
| | CHO | HWB | U-937 | HWB |
| 34 | — | 0.86 | >10 | |
| 35 | — | 0.35 | >10 | |
| 36 | — | 0.4 | 0.3–1 | |

The invention will now be illustrated by the following non-limiting examples in which, unless stated otherwise:
(i) all operations were carried out at room or ambient temperature, that is, at a temperature in the range 18°–25° C.;
(ii) evaporation of solvent was carried out using a rotary evaporator under reduced pressure (600–4000 pascals: 4.5–30 mm Hg) with a bath temperature of up to 60° C.;
(iii) the course of reactions was followed by thin layer chromatography (TLC) and reaction times are given for illustration only;
(iv) melting points are uncorrected and 'd' indicates decomposition; the melting points given are those obtained for the materials prepared as described; polymorphism may result in isolation of materials with different melting points in some preparations;
(v) the structure and purity of all final products were assured by at least one of the following techniques: TLC, mass spectrometry, nuclear magnetic resonance (NMR) spectrometry or microanalytical data;
(vi) yields are given for illustration only;
(vii) when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;
(viii) chemical symbols have their usual meanings; the following abbreviations have also been used v (volume), w (weight), b.p. (boiling point), M.P. (melting point), L (liter(s)), mL (milliliters), g (gram(s)), mg (milligrams(s)), mol (moles), mmol (millimoles), eq (equivalent(s)).

EXAMPLE 1

5-(4-Methylsulfonyl)phenyl-2-phenyl-4-phenyl-2H-pyridazin-3-one

A mixture of 5-hydroxy-4-(4-methylsulfonyl)phenyl-3-phenyl-5H-furan-2-one (330 mg, 1.0 mmol) and phenylhydrazine (150 mL, 1.5 mmol) in EtOH (5 mL) was refluxed overnight. After cooling to r.t., the mixture was diluted with H$_2$O and acidfied with aqueous 6M HCl. The precipitate formed was collected, washed with H$_2$O and dried under vacuum to give the title compound as a bright yellow powders (120 mg, 30%)

$^1$H NMR (Acetone-d$_6$) d 8.16 (s, 1H), 7.90 (d, 2H), 7.75 (d, 2H), 7.60—7.40 (m, 5H), 7.30 (m, 5H), 3.12 (s, 3H).

EXAMPLE 2

2-Methyl-5-(4-methylsulfonyl)phenyl-4-phenyl-2H-pyridazin-3-one

Following the procedure described for example 1, the title compound was prepared from 5-hydroxy-4-(4-methylsulfonyl)phenyl-3-phenyl-5H-furan-2-one and methylhydrazine.

$^1$H NMR (Acetone-d6) d 7.94 (s, 1H), 7.86 (d, 2H), 7.49 (d, 2H), 7.25 (m, 5H), 3.79 (s, 3H), 3.10 (s, 3H).

MS (FAB+): m/z 341 (M$^+$+1).

EXAMPLE 3
2-Cyclopropylmethyl-5-(4-methylsulfonyl)phenyl-4-phenyl-2H-pyridazin-3-one Step 1: 5-(4-Methylsulfonyl)phenyl-4-phenyl-2H-pyridazin-3-one A mixture of 5-hydroxy-4-(4-methylsulfonyl)phenyl-3-phenyl-5H-furan-2-one (610 mg, 1.9 mmol) and hydrazine (80 mL, 2.6 mmol) in EtOH (10 mL) was refluxed for 4 h. After cooling to r.t., the mixture was diluted with $H_2O$, acidfied with aqueous 6M HCl and stirred for 30 min. The precipitate formed was collected, washed with $H_2O$ and dried under vacuum to give the title compound as a light brown powders (460 mg, 76%)

1H NMR (Acetone-d6) d 12.32 (bs, 1H), 7.96 (s, 1H), 7.88 (d, 2H), 7.52 (d, 2H), 7.24 (m, 5H), 3.10 (s, 3H).

Step 2: 2-Cyclopropylmethyl-5-(4-methylsulfonyl)phenyl-4-phenyl-2H-pyridazin-3-one To a solution of 5-(4-methylsulfonyl)phenyl-4-phenyl-2H-pyridazin-3-one (100 mg, 0.31 mmol) in DMF (1 mL) at r.t. was added aqueous 10 M NaOH (35 mL, 0.35 mmol) followed by (bromomethyl)cyclopropane (50 mL, 0.51 mmol). The mixture was stirred at r.t. for 1 h, and then chromatographed over silica gel, eluted with hexanes:EtOAc (1:1) and swished with $Et_2O$ to give the title compound as a white powders (60 mg, 51 %).

$^1$H NMR (Acetone-$d_6$) d 7.98 (s, 1H), 7.88 (d, 2H), 7.52 (d, 2H), 7.25 (m, 5H), 4.06 (d, 2H), 3.10 (s, 1H), 1,40 (m, 1H), 0.60—0.40 (m, 4H).

MS (FAB+): m/z 381 (M$^+$+1).

EXAMPLE 4
5-(4-Methylsulfonyl)phenyl-4-phenyl-2-(2,2,2-trifluoroethyl)-2H-pyridazin-3-one Following the procedure described for example 1, the title compound was prepared from 5-hydroxy-4-(4-methylsulfonyl)phenyl-3-phenyl-5H-furan-2-one and 2,2,2-trifluoroethylhydrazine.

$^1$H NMR (Acetone-d6) d 8.09 (s, 1H), 7.88 (d, 2H), 7.54 (d, 2H), 7.25 (m, 5H), 5.00 (q, 2H), 3.11 (s, 3H).

MS (FAB$^+$): m/z 409 (M$^+$+1).

EXAMPLE 5
2-Benzyl-5-(4-methylsulfonyl)phenyl-4-phenyl-2H-pyridazin-3-one

Following the procedure described for example 3, step 2; the title compound was prepared from 5-(4-methylsulfonyl)phenyl-4-phenyl-2H-pyridazin-3-one and benzyl bromide.

$^1$H NMR (Acetoned$_6$) d 7.99 (s, 1H), 7.85 (d, 2H), 7.60—7.20 (m, 12H), 5.38 (s, 2H), 3.10 (s, 3H).

MS(FAB+):417(M$^+$+1).

EXAMPLE 6
2-Isopropyl-5-(4-methylsulfonyl)phenyl-4-phenyl-2H-pyridazin-3-one

Following the procedure described for example 3, step 2; the title compound was prepared from 5-(4-methylsulfonyl)phenyl-4-phenyl-2H-pyridazin-3-one and 2-iodopropane.

$^1$H NMR (Acetone-$d_6$) d 8.02 (s, 1H), 7.85 (d, 2H), 7.49 (d, 2H), 7.25 (m, 5H), 5.30 (m, 1H), 3.11 (s, 3H), 2.04 (d, 6H).

MS (FAB$^+$): m/z 369 (M$^+$+1).

EXAMPLE 7
2-Cyclopropylmethyl-4-(3,4-difluorophenyl)-5-(4-methylsulfonyl)phenyl-2H-pyridazin-3-one Step 1: 4-(3,4-Difluorophenyl)-5-(4-methylsulfonyl)phenyl-2H-pyridazin-3-one Following the procedure described for example 3, step 1; the title compound was prepared from 3-(3,4-difluorophenyl)-5-hydroxy-4-(4-methylsulfonyl)phenyl-5H-furan-2-one and hydrazine.

$^1$H NMR (Acetone-$d_6$) d 12.5 (bs, 1H), 7.98 (s, 1H), 7.94 (d, 2H), 7.58 (d, 2H), 7.40—6.90 (m, 3H), 3.12 (s, 3H).

Step 2: 2-Cyclopropylmethyl-4-(3,4-difluorophenyl)-5-(4-methylsulfonyl)phenyl-2H-pyridazin-3-one Following the procedure described for example 3, step 2; the title compound was prepared from 4-(3,4-difluorophenyl)-5-(4-methylsulfonyl)phenyl-2H-pyridazin-3-one and (bromomethyl)cyclopropane.

$^1$H NMR (Acetone-$d_6$) d 7.93 (s, 1H), 7.92 (d, 2H), 7.57 (d, 2H), 7.35 (m, 1H), 7.18 (m, 1H), 6.96 (m, 1H), 4.05 (d, 2H), 3.13 (s, 3H), 1.40 (m, 1H), 0.60—0.40 (ml 4H).

MS (FAB$^+$): m/z 417 (M$^+$+1).

EXAMPLE 8
5-(4-Methylsulfonyl)phenyl-4-phenyl-2-(2-p1ridylmethyl)-2H-pyridazin-3-one Following the procedure described for example 3, step 2; the title compound was prepared from 5-(4-methylsulfonyl)phenyl-4-phenyl-2H-pyridazin-3-one and 2-picolyl chloride hydrochloride (Extra base was used to neutralized the HCl salt).

$^1$H NMR (Acetone-$d_6$) d 8.52 (m, 1H), 8.02 (s, 1H), 7.88 (d, 2H), 7.76 (m, 1H), 7.54 (d, 2H), 7.38 (d, 1H), 7.25 (m, 6H), 5.50 (s, 2H), 3.10 (s, 3H).

MS (FAB$^+$): mlz 418 (M$^+$+1).

EXAMPLE 9
2-Benzyl-4-(3,4-difluorophenyl)-5-(4-methylsulfonyl)phenyl-2H-pnidazin-3-one Following the procedure described for example 3, step 2; the title compound was prepared from 4-(3,4-difluorophenyl)-5-(4-methylsulfonyl)phenyl-2H-pyridazin-3-one and benzyl bromide.

$^1$H NMR (Acetone-$d_6$) d 8.02 (s, 1H), 7.92 (d, 2H), 7.56 (d, 2H), 7.54—6.95 (m, 8H), 5.40 (s, 2H), 3.10 (s, 3H).

MS (FAB$^+$): m/z 453 (M$^+$+1).

EXAMPLE 10
2-(4-Fluorobenzyl)-5-(4-methylsulfonyl)phenyl-4-phenyl-2H-pydazin-3-one Following the procedure described for example 3, step 2, the title compound was prepared from 5-(4-methylsulfonyl)phenyl-4-phenyl-2H-pyridazin-3-one and 4-fluorobenzylbromide.

M.S. (APCI) m/z 435 (M+H)+

$^1$H NMR (CD$_3$COCD$_3$) d 3.10(3H, s), 5.37(21H, s), 7.12 (2H, t), 7.20—7.25(5H,m),7.49(2H, d), 7.55(2H, m), 7.85 (21H,d), 7.99(1H,s).

EXAMPLE 11
2-Carbomethoxymethyl-5-(4-methylsulfonyl)phenyl-4-phenyl-2H-pyridazin-3-one Following the procedure described for example 3, step 2, the title compound was prepared from 5-(4-methylsulfonyl)phenyl-4-phenyl-2H-pyridazin-3-one and methyl bromoacetate.

M.S. (A-PCI) m/z 399 (M+H)$^+$ $^1$H NMR (CD$_3$COCD$_3$) d 3.11(311, s), 3.76 (3s, 1), 4.94 (2H, s), 7.23–7.26(530m),7.53(2H, d), 7.88(2H,d), 8.11(1H, s).

EXAMPLE 12
2-Benzyl-4-(4-fluorophenyl)-5-(4-methylsulfonyl)phenyl-2H-pydazin-3-one Step 1: 4-(4-Fluorophenyl)-5-(4-methylsulfonyl)phenyl-2H-pyridazin-3-one Following the procedure described for example 3, step 1; the title compound was prepared from 3-(4-fluorophenyl)-5-hydroxy-4-(4-methylsulfonyl)phenyl-5H-furan-2-one and hydrazine.

$^1$H NMR (Acetone-d$_6$) d 12.38 ((Ms, 1), 7.95 (s, 11), 7.90 (d, 21), 7.52 (d, 21H), 7.30 (m, 2), 7.00 (m, 211), 3.12 (s, 31H).

Step 2: 2-Benzyl-4-(4-fluorophenyl)-5-(4-methylsulfonyl)phenyl-2H-pyridazin-3-one Following the procedure described for example 3, step 2; the title compound was prepared from 4-(4-fluorophenyl)-5-(4-methylsulfonyl)phenyl-2H-pyridazin-3-one and benzyl bromide.

$^1$H NMR (Acetone-d$_6$) d 8.00 (s, 1H), 7.89 (d, 2H), 7.51 (d, 2H), 7.50—7.00 (m, 9H), 5.38 (s, 2H), 3.11 (s, 3H).

MS (FAB$^+$): m/z 435 (M$^+$+1).

EXAMPLE 13

2-(4-Carbomethoxybenzyl)-5-(4-methylsulfonyl)phenyl4-phenyl-2H-pyridazin-3-one

Following the procedure described for example 3, step 2, the title compound was prepared from 5-(4-methylsulfonyl)phenyl-4-phenyl-2H-pyridazin-3-one and 4-carbomethoxybenzylbromide.

M.S. (APCI) m/z 474 (M+H)$^+$

1H NMR (CD$_3$COCD$_3$) d 3.10(3H, s), 3.87 (3H, s), 5.46 (2H, s), 7.22–7.25(5H,m), 7.50(2H, d), 7.59(2H,d), 7.86(2H, d), 8.00(3H,m).

EXAMPLE 14

2-Cyclopropylmethyl-4-(4-fluorophenyl)-5-(4-methylsulfonyl)phenyl-2H-pyridazin-3-one Following the procedure described for example 3, step 2; the title compound was prepared from 4-(4-fluorophenyl)-5-(4-methylsulfonyl)phenyl-2H-pyridazin-3-one and (bromomethyl)cyclopropane.

$^1$H NMR (Acetone-d6) d 7.97 (s, 1H), 7.89 (d, 2H), 7.52 (d, 2H), 7.28 (m, 2H), 7.00 (m, 2H), 4.05 (d, 2H), 3.11 (s, 3H), 1.40 (m, 1H), 0.60—0.40 (m, 4H).

MS (FAB$^+$): m/z 399 (M$^+$+1).

EXAMPLE 15

2-(3-Fluorobenzyl)-5-(4-methylsulfonyl)phenyl-4-phenyl-2H-pyridazin-3-one

Following the procedure described for example 3, step 2, the title compound was prepared from 5-(4-methylsulfonyl)phenyl-4-phenyl-2H-pyridazin-3-one and 3-fluorobenzyl chloride. M.S. (APCI) m/z 435 (M+H)$^+$ $^1$H NMR (CD$_3$COCD$_3$) d 3.10(3H, s), 5.40 (2H, s), 7.08(1H,m), 7.23–7.42(8H, m), 7.51(2H,d), 7.86(2H,d), 8.02 (1H,s).

EXAMPLE 16

2-(4-Fluorobenzyl)-4-(4-fluorophenyl)-5-(4-methylsulfonyl)phenyl-2H-pyridazin-3-one Following the procedure described for example 3, step 2; the title compound was prepared from 4-(4-fluorophenyl)-5-(4-methylsulfonyl)phenyl-2H-pyridazin-3-one and 4-fluorobenzyl bromide.

$^1$H NMR (Acetone-d6) d 8.00 (s, 1H), 7.89 (d, 2H), 7.60—7.00 (m, 1OH), 5.36 (s, 2H), 3.10 (s, 3H).

MS (FAB$^+$): m/z 453 (M$^+$+1).

EXAMPLE 17

2-(2-Fluorobenzyl)-5-(4-methylsulfonyl)phenyl-4-phenyl-2H-pyridazin-3-one

Following the procedure described for example 3, step 2, the title compound was prepared from 5-(4-methylsulfonyl)phenyl-4-phenyl-2H-pyridazin-3-one and 2-fluorobenzyl chloride.

M.S. (APCI) m/z 435 (M+H)$^+$, M.P. 167° C.

$^1$H NMR (CD$_3$COCD$_3$) d 3.10(3H, s), 5.46 (2H, s),7.17–7.25(7H, m), 7.37(1H,m), 7.46(1H,m), 7.52 (2H, d), 7.86(2H,d), 8.00(1H,s).

EXAMPLE 18

2-Cyclopropyl-5-(4-methylsulfonyl)phenyl-4-(4-fluorophenyl)-2-H-pyridazin-3-one

Following the procedure described for example 1, the title compound was prepared from 3-(4-fluorophenyl)-5H-furan-2-one and cyclopropylhydrazine hydrochloride (Et3N was used to neutralize the Hcl salt)

$^1$H NMR (Acetone-d$_6$) d 7.81 (s, 1H), 7.77 (d, 2H), 7.52 (m, 2H), 7.43 (d, 2H), 7.30 (m, 2H), 3.50 (m, 1H), 3.06 (s, 3H), 1.10 (m, 2H), 0.88 (m, 2H).

EXAMPLE 19

4-(4-Fluorophenyl)-5-(4-methylsulfonyl)phenyl-2-(3.3,3-trifluoropropyl)-2H-pyridazin-3-one Following the procedure described for example 3, step 2, the title compound was prepared from 5-(4-methylsulfonyl)phenyl-4-(4-fluorophenyl)-2H-pyridazin-3-one and 3,3,3-trifluoropropyl iodode.

M.S. (APCI) m/z 441 (M+H)$^+$, $^1$H NMR (CD$_3$COCD$_3$) d 2.87(2H, m), 3.11(3H, s), 4.48 (2H, t),7.03(2H, t), 7.29(2H,dd), 7.89(2H,d), 8.03(1H,s).

EXAMPLE 20

4-(4-Fluorophenyl)5-(4-methylsulfonyl)phenyl-2-(4-pyridylmethyl)-2H-pyridazin-3-one Following the procedure described for example 3, step 2, the title compound was prepared from 5-(4-methylsulfonyl)phenyl-4-(4-fluorophenyl)-2H-pyridazin-3-one and 4-chloromethylpyridine hydrochloride.

M.S. (APCI) m/z 436 (M+H)$^+$, $^1$H NMR (CD$_3$COCD$_3$) d 3.11(3H, s), 5.42 (2H, s),7.02 (2H, t), 7.28(2H,dd), 7.37(2H,d), 7.53(2H,d), 7.90(2H,d), 8.04(1H,s), 8.54(2H,d)

EXAMPLE 21

2-Benzyl-4-(2-propoxy)-5-(4-methylsulfonyl)phenyl-2H-pyridazin-3-one

Step 1: 2-benzyl-4.5-dibromo-2H-pyridazin-3-one

A mixture of 4,5-dibromopyridazin-2H-pyridazin-3-one (10 g, 40 mmol), benzyl bromide (6.84 g, 40 mmol), 8N KOH (5 mL, 40 mmol) and DMF (40 mL) was warmed up to 50° C. and reacted for 0.5 hr. The mixture was cooled to r.t., poured over H20 (500 mL) and extracted twice with Et$_2$O (200 mL). The combined organic layers were washed with brine, dried with MgSO$_4$ and the solvent was removed in vacuo to give the title compound which was used for next step without further purification.

Alternatively, a suspension of mucobromic acid (80 g., 310 mmol.) and benzylhydrazine dihydrochloride (60 g., 310 mmol.) in ethanol was heated to reflux for 16 hours. It was cooled to r.t. and under vigourous stirring water (50 mL) was added. The suspension was cooled in an ice bath and then filtered. The solid was washed with 95% aqueous ethanol and air dried. It was swished in hexanes (200 mL) and diethyl ether (25 mL), filtered and air dried to yield the title compound(58 g.).

$^1$H NMR (CD$_3$COCD$_3$) d 5.30(2H, s), 7.20–7.40(5H, m), 8.0(1H, s).

Step 2: 2-benzyl-4-bromo-5-hydroxy-2H-pyridazin-3-one

The residue from step 1 was dissolved in HMPA (50 mL) and 8N KOH (65 mL) was added. The mixture was warmed to 120°–125° C. and stirred vigourously for 16 h. The mixture was cooled to r.t., the aqueous layer was separated, diluted with H$_2$O (500 mL) and acidified to pH 6 with 6N HCl under vigourous stirring. After cooling in an ice bath, the solid was collected and air dried. It was dissolved in warm 1N NaOH and washed once with ETOAc. The aqueous layer was acidified to pH 6 with 6N HCl and cooled again in an ice bath. The solid was filtered and air dried to yield the title compound (4.4 g, 40 %).

1H NMR (CD$_3$SOCD$_3$) d 5.20(2H, s), 7.20-7.35(5H, m), 7.75(1H, s), 12.0–12.4(1H, bs).

Step 3: 2-Benzgl-4-bromo-5-(4-methylthio)phenyl-2H-pyridazin-3-one

To a 0° C. solution of the alcohol from step 2 (4.4 g, 16.6 mmol), triethylamine (3 mL, 22 mmol) and dichloromethane (80 mL) was added dropwise triluoromethanesulfonic anhydride (3.2 mL, 19 mmol) and the mixture was reacted at 0° C. for 1.5 h. The mixture was poured over icy dilute HCl and extracted twice with CH$_2$Cl$_2$. The combined organic layers were washed with 10% NaHCO$_3$, brine, dried with MgSO$_4$ and the solvent was removed in vacuo to yield the sulfonate derivative which was used immediately. A suspension of the sulfonate, 4-(methylthio)phenyl boronic acid (3.1 g, 18.5 mmol), 2M Na$_2$CO$_3$ (18.5 mL) and THF (100 mL) was degassed by passing a flow of nitrogen into the suspension for 0.25 h. and Pd(PPh$_3$)$_4$ (1.09 g, 0.95 mmol) was added. The mixture was heated to reflux under N2 for 1.5 h and then cooled to r.t. It was poured over water (300 mL) and extracted twice with EtOAc. The combined organic layers were washed with brine, dried with MgSO$_4$ and the solvent was removed in vacuo. The residue was purified by chromatography on SiO$_2$ using EtOAc and hexanes (1:5) and yielded the title compound (2.37 g, 37%).

$^1$H NMR (CD$_3$COCD$_3$) d 2.55(3H, s), 5.35(2H, s), 7.25–7.55(9H, m), 7.80(1H, d).

Step 4: 2-Benzyl-4-bromo-5-(4-methylsulfonyl)phenyl-2H-pyridazin-3-one

To a 0° C. suspension of the sulfide from step 3 (2.36 g, 6.09 mmol) in CH$_2$Cl$_2$ (30 mL) and methanol (30 mL) was added magnesium monoperoxyphthlate (4 g, 6.5 mmol) and the mixture was slowly warmed up to r.t. and stirred for 16 h. It was poured over icy H$_2$O (200 mL) and extracted twice with CH$_2$Cl$_2$. The combined organic layers were washed with 10% NaHCO$_3$, brine, dried with MgSO$_4$ and the solvent was removed in vacuo to yield the essentially pure title compound (1.72 g, 68 %).

$^1$H NMR (CD$_3$COCD$_3$) d 3.20(3H, s), 5.40(2H, s), 7.20–7.50(5H, m), 7.80–7.90(3H, m), 8.10–8.20(2H, m).

Step 5: 2-Benzyl-4-(2-propoxy)-5-(4-methylsulfonyl)phenyl-2H-pyridazin-3-one

A suspension of the bromide from step 4 (0.419 g, 1 mmol), isopropanol (1 mL), in DMF (5. mL) and Cs$_2$CO$_3$ (0.975 g, 3 mmol) was warmed to 70°–80° C. and reacted for 3 h. It was cooled to r.t., poured over H$_2$O (20 mL) and extracted twice with EtOAc. The combined organic layers were washed with brine, dried with MgSO$_4$ and the solvent was removed in vacuo. The residue was purified by chromatography on SiO$_2$ using EtOAc and hexanes (1:1) and swished in Et$_2$O to yield the title compound (0.12 g, 30%).

$^1$H NMR (CD$_3$COCD$_3$) d 1.10–1.20(6H, d) 3.20(3H, s), 5.30(2H, s), 5.40–5.60(1H, m) 7.20–7.50(5H1, m), 7.85–8.10(5H, m).

MS(CI, CH$_4$): m/z 399 (M+H)$^+$

EXAMPLE 22

2-Benzyl-4-(4-fluorophenoxy)-5-(4-methylsulfonyl)phenyl-2H-pyridazin-3-one

A suspension of the bromide from step 4, Example 21 (0.419 g, 1 mmol), 4-fluorophenol (0.135 g, 1.2 mmol), DMF (5 mL) and Cs$_2$CO$_3$ (0.975 g, 3 mmol) was warmed to 70°–80° C. and reacted for 3 h. It was cooled to r.t., poured over H$_2$O (20 mL) and extracted twice with EtOAc. The combined organic layers were washed with brine, dried with MgSO$_4$ and the solvent was removed in vacuo. The residue was purified by chromatography on SiO$_2$ using EtOAc and hexanes (1:1) and swished in Et$_2$O to yielded the title compound (0.22 g, 49 %).

$^1$H NMR (CD$_3$COCD$_3$) d 3.15(3H, s), 5.30(2H, s), 6.95–7.45(9H, m), 7.90(2H, m), 8.05(2H, m), 8.15(1H,s).

MS(CI, CH$_4$): m/z 451 (M+H)$^+$

EXAMPLE 23

2-Benzyl-4-(5-chloro-2-pyridyloxy)-5-(4-methylsulfonyl)phenyl-2H-pyridazin-3-one A suspension of the bromide from step 4, Example 21 (0.419 g, 1 mmol), 5-chloro-2-pyridinol (0.194 g, 1.5 mmol), CH3CN (5 mL) and DBU (0.304 g, 2 mmol) was warmed to 70°–80° C. and reacted for 4 h. It was cooled to r.t., poured over H$_2$O (20 mL) and extracted twice with EtOAc. The combined organic layers were washed with brine, dried with MgSO$_4$ and the solvent was removed in vacuo. The residue was purified by chromatography on SiO$_2$ using EtOH and EtOAc (1:100) to yield a mixture of the O-linked and N-linked derivatives. The mixture was again purified by chromatography on SiO$_2$ using EtOAc and hexanes (1:2) to yield the title compound (0.038 g, 8%).

$^1$H NMR (CD$_3$COCD$_3$) d 3.15(3H, s), 5.30(2H, s), 7.10 (1H,m),7.25–7.45(5H, m), 7.90(3H, m), 8.05(2H, m), 8.10 (1H,s), 8.15(1H,s).

MS(CI, CH$_4$): m/z 468 (M+H)$^+$

EXAMPLE 24

2-(2,2-Dimethylpropyl)-4-(4-fluorophenyl)-5-(4-methylsulfonyl)phenyl-2H-pyridazin-3-one Following the procedure described for example 3, step 2, using cesium carbonate as a base,the title compound was prepared from 5-(4-methylsulfonyl)phenyl-4-(4-fluorophenyl)-2H-pyridazin-3-one and 2,2-dimethylpropyl bromide.

$^1$H NMR (CD$_3$COCD$_3$) d 1.03(9H, s),3.11(3H, s), 4.09 (2H, s),7.02(2H, t), 7.27(2H,dd), 7.52(2H,d), 7.89(2H,d), 7.97(1H,s)

EXAMPLE 25

4-(4-Fluorophenyl)-5-(4-methylsulfonyl)phenyl-2-(1-phenyl-ethyl)-2H-pyridazin-3-one Following the procedure described for example 3, step 2; the title compound was prepared from 4-(4-fluorophenyl)-5-(4-methylsulfonyl)phenyl-2H-pyridazin-3-one and (1-bromoethyl)benzene.

$^1$H NMR (Acetone-d$_6$) d 8.04 (s, 1H), 7.88 (d, 2H), 7.55—7.20 (m, 9H), 7.00 (m, 2H), 6.37 (q, 1H), 3.11 (s, 3H), 1.81 (d, 3H).

MS (FAB$^+$): m/z 449 (M$^+$+1).

EXAMPLE 26

2-(3-Fluorophenyl)-5-(4-methylsulfonyl)phenyl-4-phenyl-2H-pyridazin-3-one

Following the procedure described for example 1, the title compound was prepared from 5-hydroxy-4-(4-methylsulfonyl)phenyl-3-phenyl- 5H-furan-2-one and 3-fluorophenylhydrazine hydrochloride (Et$_3$N was used to neutralized the HCl salt.).

$^1$H NMR (Acetone-d6) d 8.16 (s, 1H), 7.90 (d, 2H), 7.60 (m, 5H), 7.35—7.15 (m, 6H), 3.12 (s, 3H).

MS (FAB$^+$): m/z 421 (M$^+$+1).

EXAMPLE 27

4-(4-Fluorophenyl)-5-(4-methylsulfonyl)phenyl-2-(thiophen-2-yl-methyl)-2H-pyridazin-3-one Following the procedure described for example 3, step 2, using cesium carbonate as a base, the title compound was prepared from 5-(4-methylsulfonyl)phenyl-4-(4-fluorophenyl)-2H-pyridazin-3-one and 2-bromomethylthiophene.

M.S. (APCI) m/z 441 (M+H)$^+$,
$^1$H NMR (CD$_3$COCD$_3$) d 3.11(3H, s), 5.53 (2H, s), 7.02 (3H, m), 7.26(3H,m), 7.42(1H,d), 7.53(2H,d), 7.89(2H,d), 7.99(1H,s)

EXAMPLE 28
2-Benzyl-5-(4-methylsulfonyl)phenyl-4-(3-pyridyl)-2H-pyridazin-3-one Step 1: Lithium Tri-2-propoxy-3-pyridinylboronate To a solution of 3-bromopyridine (39.5 g) in ether (800 mL) at −90° C. (internal temperature) was added n-BuLi (100 mL, 2.5 M) at a rate so that the internal temperature did not exceed −78° C. The resulting mixture was stirred for 1 h at −78° C. and then triisopropoxy-borate (59 mL) was added and the resulting mixture was warmed to 0° C. Methanol was added and the mixture was evaporated three times from methanol and then two times from n-propanol. The residue was pumped under high vacuum for 3 days and the resulting foam (76 g of a 1:1 mixture of the title compound:n-propanol) was used as such in the subsequent reaction.

Step 2: 2-Benzyl-5-(4-methylsulfonyl)phenyl-4-(3-pyridyl)-2H-pyridazin-3-one

A solution of 2-benzyl-4-bromo-5-(4-methylsulfonyl)phenyl-2H-pyridazin-3-one, example 21, step 3 (50 mg), [1,1'-bis(diphenylphosphino)-ferrocene]dichloropalladium (II), dichloromethane complex (5 mg), lithium tri-2-propoxy-3-pyridinylboronate (39 mg) in N,N-dimethylformamide (1 mL) and 2M Na$_2$CO$_3$ (0.25mL) was cooled in a dry ice-acetone bath and pumped under high vacuum for 5 min. then th mixture was left to warm up to R.T., this process was repeated 2 times. The solution was then heated at 80° C. for 45 min. The mixture was extracted with ethyl acetate, washed with brine (3×), dried over magnesium sulfate, filtered and the solvent evaporated under vacuum. Purification by silica gel chromatography afforded 26 mg of the title compound.

M.S. (APCI) m/z 418 (M+H)$^+$,
$^1$H NMR (CD$_3$COCD$_3$) d 3.11(3H, s), 5.39 (2H, s), 7.27–7.38(4H, m), 7.50(2H,d), 7.56(2H,d), 7.69(1H,d), 7.91(2H,d), 8.04(1H,s)8.35(1H,s)8.46(1H,d)

EXAMPLE 29
4-(4-Fluorophenyl)-5-(4-methylsulfonyl)phenyl-2-(4,4,4-trifluorobutyl)-2H-pyridazin-3-one Following the procedure described for example 3, step 2, using -cesium carbonate as a base, the title compound was prepared from 5-(4-methylsulfonyl)phenyl-4-(4-fluorophenyl)-2H-pyridazin-3-one and 4,4,4-trifluorobutyl iodode.

M.S. (APCI) m/z 455 (M+H)$^+$, M.P. 125° C.
$^1$H NMR (CD$_3$COCD$_3$) d 2.12(2H, m), 2.39(2H, m)3.11 (3H, s), 4.32 (2H, t), 7.04(2H, t), 7.28(2H,dd), 7.52(2H,d), 7.90(2H,d),8.01(1H,s)

EXAMPLE 30
2-Benzyl-4-(6-methyl-3-pyridyl)-5-(4-methylsulfonyl)phenyl-2H-pyridazin-3-one Step 1: Lithium Tri-2-propoxy-5-methyl-2-pyridylboronate Following the procedures described in Example 28, Step 1 but substituting 2-bromo-5-methylpyridine for 3-bromopyridine, the title compound was obtained.

Step 2: Following the procedure described for example 28, the title compound was prepared using lithium (tri-2-propoxy)-5-methyl-2-pyridylboronate M.S. (APCI) m/z 432 (M+H)$^+$, M.P. 155.70C.
$^1$H NMR (CD$_3$COCD$_3$) d 2.43(3H, s), 3.12(3H, s), 5.39 (2H, s),7.14(1H, d), 7.29–7.37(3H,m), 7.49(2H,d), 7.56(3H, d), 7.91(2H,d), 8.00(1H,s),8.23(1H,s)

EXAMPLE 31
4-(4-Fluorophenyl)-2-(2-methylpropyl)-5-(4-methylsulfonyl)phenyl-2H-pyridazin-3-one Following the procedure described for example 3, step 2, using cesium carbonate as a base, the title compound was prepared from 5-(4-methylsulfonyl)phenyl-4-(4-fluorophenyl)-2H-pyridazin-3-one and 2-methylpropyl iodide.

M.S. (APCI) m/z 401 (M+H)$^+$, M.P. 120.0° C.
$^1$H NMR (CD$_3$COCD$_3$) d 0.97(6H, d), 2.30(1H, m), 3.11(3H, s),4.02(2H, d), 7.01 (2H, t),7.27(2H, t), 7.51(2H,d), 7.89(2H,d), 7.97(1H,s).

EXAMPLE 32
2-Cyclobutylmethyl-4-(4-fluorophenyl)-5-(4-methylsulfonyl)phenyl-2H-pyridazin-3-one Following the procedure described for example 3, step 2, using cesium carbonate as a base, the title compound was prepared from 5-(4-methylsulfonyl)phenyl-4-(4-fluorophenyl)-2H-pyridazin-3-one and bromomethylcyclobutane.

M.S. (APCI) m/z 413 (M+H)$^+$, M.P. 168.1° C.
$^1$H NMR (CD$_3$COCD$_3$) d 1.93(6H, m),2.92(1H, m), 3.11 (3H, s), 4.23 (2H, d), 7.02(2H,t), 7.28(2H,dd), 7.50(2H,d), 7.89(2H,d), 7.95(1H,s)

EXAMPLE 33
2-(2-Phenethyl)-4-(4-fluorophenyl)-5-(4-methylsulfonyl)phenyl-2H-pyridazin-3-one Following the procedure described for example 3, step 2, using cesium carbonate as a base, the title compound was prepared from 5-(4-methylsulfonyl)phenyl-4-(4-fluorophenyl)-72H-pyridazin-3-one and 2-phenylethyl bromide.

M.S. (APCI) m/z 449 (M+H)$^+$, M.P. 172.1° C.
$^1$H NMR (CD$_3$COCD$_3$) d 3.11(3H, s),3.15(2H, t), 4.42 (2H, t),7.02(2H, t), 7.22–7.32(7H,m), 7.50(2H,d), 7.89(2H, d), 7.96(1H,s)

EXAMPLE 34
2-Benzyl-4-(5-bromo-2-pyridyloxy)-5-(4-methylsulfonyl)phenyl-2H-pyridazin-3-one A suspension of the bromide from step 4, Example 21 (0.419 g, 1 mmol), the potassium salt of 5-bromo-2-pyridinol (0.424 g, 2.0 mmol) in DMF (5 mL) was warmed to 65° C. and reacted for 3 h. It was cooled to r.t., poured over H$_2$O (20 mL) and extracted twice with EtOAc. The combined organic layers were washed with brine, dried with MgSO$_4$ and the solvent was removed in vacuo. The residue was purified by chromatography on SiO$_2$ using EtOAc and hexanes (1:1) and swished in Et$_2$O to yield the title compound (0.285 g, 56%).

$^1$H NMR (CD$_3$COCD$_3$) d 3.15(3H, s), 5.45(2H, s), 7.10 (1H,m),7.25–7.45(5H, m), 7.90(2H, m), 8.00(3H, m), 8.10 (1H,s), 8.20(1H,s).

EXAMPLE 35
2-Benzyl-4-(4-methylphenyl)-5-(4-methylsulfonyl)phenyl-2H-pyridazin-3-one Following the procedure described for example 28, the title compound was prepared using 14-methyl boronic acid.

M.S. (APCI) m/z 431 (M+H)$^+$, M.P. 179.6° C.
$^1$H NMR (CD$_3$COCD$_3$) d 2.12(3H, s), 3.08(3H, s),5.39 (2H, s), 6.92 (1H, d),7.01(1H, m), 7.17(2H,d), 7.28–7.37 (3H,m), 7.47(4H,m), 7.83(2H,d), 8.02(1H,s)

EXAMPLE 36

2-Cycloheylmethyl-4-(4-fluorophenyl)-5-(4-methylsulfonyl)phenyl-2H-pyridazin-3-one Following the procedure described for example 3, step 2, using cesium carbonate as a base, the title compound was prepared from 5-(4-methylsulfonyl)phenyl-4-(4-fluorophenyl)-2H-pyridazin-3-one and bromomethylcyclohexane.

M.S. (APCI) m/z 441 (M+H)+, M.P. 175.1° C.

$^1$H NMR (CD$_3$COCD$_3$) d 1.03–1.28(6H, m), 1.64–1.76 (5H, m), 3.11(3H, 15 s),4.04(2H, d), 7.01 (2H, t),7.27(2H, m), 7.51(2H,d), 7.89(2H,d), 7.96(1H,s).

What is claimed is:

1. A compound of formula I:

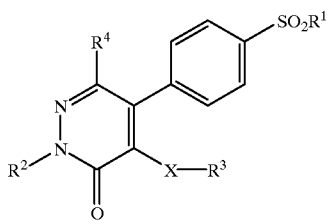

or a pharmaceutically acceptable salt or hydrate thereof wherein:

X is selected from the group consisting of
  (a) a bond,
  (b) (CH$_2$)$_m$, m=1 or 2,
  (c) CO,
  (d) O,
  (e) S, and
  (f) N(R$^5$),
R$^1$ is selected from the group consisting of
  (a) CH$_3$,
  (b) NH$_2$,
  (c) NHC(O)CF$_3$,
R$^2$ is selected from the group (CR$^6$R$^7$)$_n$R$^8$, n=0, 1, 2; where
  R$^6$, R$^7$ are each independently selected from the group consisting of
    (a) hydrogen,
    (b) C$_{1-10}$ alkyl,
    (c) C$_{1-10}$ fluoroalkyl,
  R$^8$ is selected from the group consisting of
    (a) C$_{1-10}$-alkyl,
    (b) mono-, di- or tri-substituted phenyl or naphthyl wherein the substituents are selected from the group consisting of
      (1) hydrogen,
      (2) halo,
      (3) C$_{1-10}$alkoxy,
      (4) C$_{1-10}$alkylthio,
      (5) CN,
      (6) C$_{1-6}$ fluoroalkyl
      (7) C$_{1-10}$ alkyl,
      (8) N$_3$,
    (c) mono- , di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a: monocyclic ring of 6 atoms, said ring having one hetero atom which is N, wherein the substituents are selected from the group consisting of
      (1) hydrogen,
      (2) halo,
      (3) C$_{1-10}$alkoxy,
      (4) C$_{1-10}$alkylthio,
      (5) CN,
      (6) C$_{1-6}$ fluoroalkyl
      (7) C$_{1-10}$ alkyl,
      (8) N$_3$,
R$^3$ is selected from the group consisting of
  (a) C$_{1-10}$alkyl,
  (b) mono-, di- or tri-substituted phenyl or naphthyl wherein the substituents are selected from the group consisting of
    (1) hydrogen,
    (2) halo,
    (3) C$_{1-10}$alkoxy,
    (4) C$_{1-10}$alkylthio,
    (5) CN,
    (6) C$_{1-6}$ fluoroalkyl
    (7) C$_{1-10}$alkyl,
    (8) N$_3$,
  (c) mono-, di- or tri-substituted heteroaryl wherein the heteroaryl is a monocyclic aromatic ring of 5 atoms, said ring having one hetero atom which is S, O, or N; or the heteroaryl is a monocyclic ring of 6 atoms, said ring having one hetero atom which is N, wherein the substituents are selected from the group consisting of
    (1) hydrogen,
    (2) halo,
    (3) C$_{1-10}$oalkoxy,
    (4) C$_{1-10}$alkylthio,
    (5) CN,
    (6) C$_{1-6}$ fluoroalkyl
    (7) C$_{1-10}$ alkyl,
    (8) N$_3$,
R$^4$ is selected from the group consisting of
  (a) hydrogen,
  (b) halo,
  (c) C$_{1-6}$alkyl,
R$^5$ is selected from the group consisting of
  (a) hydrogen,
  (b) C$_{1-6}$alkyl.

2. A compound according to claim 1 wherein X is a bond.

3. A compound according to claim 1 wherein X is O.

4. A compound according to claim 1 wherein R$^1$ is CH$_3$.

5. A compound according to claim 1 wherein R$^4$ is hydrogen.

6. A compound according to claim 1 wherein n is 1.

7. A compound according to claim 1 wherein R$^6$ and R$^7$ are each independently hydrogen.

8. A compound according to claim 1 wherein R$^8$ is mono, di- or tri-substituted phenyl.

9. A compound according to claim 1 wherein X is selected from the group consisting of
  (a) a bond,
  (b) O,
R$^1$ is selected from the group consisting of
  (a) CH$_3$,
  (b) NH$_2$,
R$^2$ is selected from the group (CR$^6$R$^7$)$_n$R$^8$, n=0 or 1, where R⁶, R⁷ are each independently selected from the group consisting of
(a) hydrogen,
(b) $C_{1-4}$alkyl,
R⁸ is selected from the group consisting of
(a) $C_{1-4}$alkyl,
(b) mono-, di- or tri-substituted phenyl or naphthyl wherein the substituents are selected from the group consisting of
  (1) hydrogen,
  (2) halo,
  (3) $C_{1-4}$alkoxy,
  (4) $C_{1-4}$alkylthio,
  (5) CN,
  (6) $C_{1-4}$fluoroalkyl
  (7) $C_{1-4}$alkyl,
(c) mono-, di- or tri-substituted heteroaryl wherein the heteroaryl is a monocyclic ring of 6 atoms, said ring having one hetero atom which is N, wherein the substituents are selected from the group consisting of
  (1) hydrogen,
  (2) halo,
  (3) $C_{1-4}$alkoxy,
  (4) $C_{1-4}$alkylthio,
  (5) CN,
  (6) $C_{1-4}$ fluoroalkyl
  (7) $C_{1-4}$ alkyl,
R³ is selected from the group consisting of
(a) $C_{1-6}$alkyl,
(b) mono-, di- or tri-substituted phenyl or naphthyl wherein the substituents are selected from the group consisting of
  (1) hydrogen,
  (2) halo,
  (3) $C_{1-4}$alkoxy,
  (4) $C_{1-4}$alkylthio,
  (5) CN,
  (6) $C_{1-4}$ fluoroalkyl
  (7) $C_{1-4}$ alkyl
  (8) $N_3$,
(c) mono-, di- or tri-substituted heteroaryl wherein the heteroaryl is a monocyclic ring of 6 atoms, said ring having one hetero atom which is N, and optionally 1, 2, or 3 additional N atoms, wherein the substituents are selected from the group consisting of
  (1) hydrogen,
  (2) halo,
  (3) $C_{1-4}$alkoxy,
  (4) $C_{1-4}$alkylthio,
  (5) CN,
  (6) $C_{1-4}$ fluoroalkyl
  (7) $C_{1-4}$ alkyl,
R⁴ is selected from the group consisting of
(a) hydrogen,
(b) halo,
(c) $C_{1-6}$alkyl.

10. A compound according to claim 9 wherein
X is selected from the group consisting of
(a) a bond,
(b) O,
R¹ is selected from the group consisting of
(a) $CH_3$,
(b) $NH_2$,
R² is selected from the group $(CH_2)nR^8$, n=0 or 1, where
R⁸ is selected from the group consisting of
(a) $C_{1-3}$alkyl,
(b) mono-, di- or tri-substituted phenyl or naphthyl wherein the substituents are selected from the group consisting of
  (1) hydrogen,
  (2) halo,
  (3) $C_{1-4}$alkoxy,
  (4) $C_{1-4}$alkylthio,
  (5) CN,
  (6) $C_{1-4}$fluoroalkyl
  (7) $C_{1-4}$alkyl,
(c) mono-, di- or tri-substituted heteroaryl wherein the heteroaryl is a monocyclic ring of 6 atoms, said ring having one hetero atom which is N, and optionally 1, 2, or 3 additional N atoms, wherein the substituents are selected from the group consisting of
  (1) hydrogen,
  (2) halo,
  (3) $C_{1-3}$alkoxy,
  (4) $C_{1-3}$ fluoroalkyl
  (5) $C_{1-3}$ alkyl,
R³ is selected from the group consisting of
(a) $C_{1-4}$alkyl,
(b) mono-, di- or tri-substituted phenyl or naphthyl wherein the substituents are selected from the group consisting of
  (1) hydrogen,
  (2) halo,
  (3) $C_{1-3}$alkoxy,
  (4) $C_{1-3}$ fluoroalkyl
  (5) $C_{1-3}$ alkyl,
(c) mono-, di- or tri-substituted heteroaryl wherein the heteroaryl is a IAonocyclic ring of 6 atoms, said ring having one hetero atom which is N, wherein the substituents are selected from the group consisting of
  (1) hydrogen,
  (2) halo,
  (3) $C_{1-3}$alkoxy,
  (4) $C_{1-3}$ fluoroalkyl
  (5) $C_{1-3}$ alkyl,
R⁴ is selected from the group consisting of
(a) hydrogen,
(b) halo,
(c) methyl.

11. A compound of formula I:

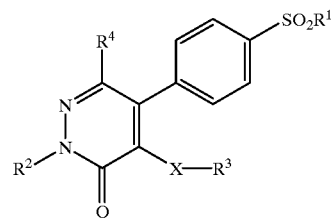

or a pharmaceutically acceptable salt or hydrate thereof, wherein
X is selected from the group consisting of
(a) a bond, or
(b) O
R¹ is $CH_3$,
R² is selected from the group $-CH_2R^8$, where
R⁸ is selected from the group consisting of mono-, di- or tri-substituted phenyl or naphthyl wherein the substituents are selected from the group consisting of
(1) hydrogen, (2) halo,
(3) $C_{1-3}$alkyl, $R^3$ is selected from the group consisting of
(a) $C_{1-4}$alkyl
(b) mono-, di- or tri-substituted phenyl or naphthyl wherein the substituents are selected from the group consisting of
(1) hydrogen,
(2) halo,
(3) $C_{1-3}$alkyl, and $R^4$ is hydrogen.

12. A compound selected from the group consisting of
(1) 5-(4-Methylsulfonyl)phenyl-2-phenyl-4-phenyl-2H-pyridazin-3-one,
(2) 2-Methyl-5-(4-methylsulfonyl)phenyl-4-phenyl-2H-pyridazin-3-one,
(3) 2-Cyclopropylmethyl-5-(4-methylsulfonyl)phenyl-4-phenyl-2H-pyridazin-3-one,
(4) 5-(4-Methylsulfonyl)phenyl-4-phenyl-2-(2,2,2-trifluoroethyl)-2H-pyridazin-3-one,
(5) 2-Benzyl-5-(4-methylsulfonyl)phenyl-4-phenyl-2H-pyridazin-3-one,
(6) 2-Isopropyl-5-(4-methylsulfonyl)phenyl-4-phenyl-2H-pyridazin-3-one,
(7) 2-Cyclopropylmethyl-4-(3,4-difluorophenyl)-5-(4-methylsulfonyl)phenyl-2H-pyridazin-3-one,
(8) 5-(4-Methylsulfonyl)phenyl-4-phenyl-2-(2-pyridylmethyl)-2H-pyridazin-3-one,
(9) 2-Benzyl-4-(3,4-difluorophenyl)-5-(4-methylsulfonyl)phenyl-2H-pyridazin-3-one,
(10) 2-(4-Fluorobenzyl)-5-(4-methylsulfonyl)phenyl-4-phenyl-2H-pyridazin-3-one,
(11) 2-Carbomethoxymethyl-5-(4-methylsulfonyl)phenyl-4-phenyl-2H-pyridazin-3-one,
(12) 2-Benzyl-4-(4-fluorophenyl)-5-(4-methylsulfonyl)phenyl-2H-pyridazin-3-one,
(13) 2-(4-Carbomethoxybenzyl)-5-(4-methylsulfonyl)phenyl-4-phenyl-2H-pyiidazin-3-one,
(14) 2-Cyclopropylmethyl-4-(4-fluorophenyl)-5-(4-methylsulfonyl)phenyl-2H-pyridazin-3-one,
(15) 2-(3-Fluorobenzyl)-5-(4-methylsulfonyl)phenyl-4-phenyl-2H-pyridazin-3-one,
(16) 2-(4-Fluorobenzyl)- 4-(4-fluorophenyl)-5-(4-methylsulfonyl)phenyl-2H-pyridazin-3-one,
(17) 2-(2-Fluorobenzyl)-5-(4-methylsulfonyl)phenyl-4-phenyl-2H-pyridazin-3-one,
(18) 2-Cyclopropyl-5-(4-methylsulfonyl)phenyl-4-(4-fluorophenyl)-2H-pyridazin-3-one,
(19) 4-(4-Fluorophenyl)-5-(4-methylsulfonyl)phenyl-2-(3,3,3-trifluoropropyl)-2H-pyridazin-3-one,
(20) 4-(4-Fluorophenyl)-5-(4-methylsulfonyl)phenyl-2-(4-pyridylmethyl)-2H-pyridazin-3-one,
(21) 2-Benzyl-4-(2-propoxy)-5-(4-methylsulfonyl)phenyl-2H-pyridazin-3-one,
(22) 2-Benzyl-4-(4-fluorophenoxy)-5-(4-methylsulfonyl)phenyl-2H-pyridazin-3-one,
(23) 2-Benzyl-4-(5-chloro-2-pyridyloxy)-5-(4-methylsulfonyl)phenyl-2H-pyridazin-3-one,
(24) 2-(2,2-Dimethylpropyl)-4-(4-fluorophenyl)-5-(4-methylsulfonyl)phenyl-2H-pyridazin-3-one,
(25) 4-(4-Fluorophenyl)-5-(4-methylsulfonyl)phenyl-2-(1-phenyl-ethyl)- 2H-pyridazin-3-one,
(26) 2-(3-Fluorophenyl)-5-(4-methylsulfonyl)phenyl-4-phenyl-2H-pyridazin-3-one,
(27) 4-(4-Fluorophenyl)-5-(4-methylsulfonyl)phenyl-2-(thiophen-2-yl-methyl)-2H-pyridazin-3-one,
(28) 2-Benzyl-5-(4-methylsulfonyl)phenyl-4-(3-pyridyl)-2H-pyridazin-3-one,
(29) 4-(4-Fluorophenyl)-5-(4-methylsulfonyl)phenyl-2-(4,4,4-trifluorobutyl)-2H-pyridazin-3 -one,
(30) 2-Benzyl-4-(6-methyl-3-pyricdyl)-5-(4-methylsulfonyl)phenyl-2H-pyridazin-3-one,
(31) 4-(4-Fluorophenyl)-2-(2-methylpropyl)-5-(4-methylsulfonyl)phenyl-2H-pyridazin-3-one,
(32) 2-Cyclobutylmethyl-4-(4-fluorophenyl)-5-(4-methylsulfonyl)phenyl-2H-pyridazin-3-one,
(33) 2-(2-Phenethyl)-4-(4-fluorophenyl)-5-(4-methylsulfonyl)phenyl-2H-pyridazin-3-one,
(34) 2-Benzyl-4-(5-bromo-2-pyridyloxy)-5-(4-methylsulfonyl)phenyl-2H-pyridazin-3-one,
(35) 2-Benzyl-4-(4-methylphenyl)-5-(4-methylsulfonyl)phenyl-2H-pyridazin-3-one, and
(36) 2-Cyclohexylmethyl-4-(4-fluorophenyl)-5-(4-methylsulfonyl)phenyl-2H-pyridazin-3-one.

13. A pharmaceutical composition comprising:
a non-toxic therapeutically effective amount of a compound according to claim 12 and a pharmaceutically acceptable carrier.

14. A method of treating an inflammatory disease susceptible to treatment with an non-steroidal anti-inflammatory agent comprising:
administration to a patient in need of such treatment of a non-toxic therapeutically effective amount of a compound according to claim 1 and a pharmaceutically acceptable carrier.

15. A pharmaceutical composition comprising a compound of claim 1 and a pharmaceutically acceptable carrier.

* * * * *